(12) United States Patent
Candelore

(10) Patent No.: US 12,161,774 B2
(45) Date of Patent: Dec. 10, 2024

(54) APPARATUS AND METHOD FOR DISINFECTION OF OBJECT

(71) Applicant: SONY GROUP CORPORATION, Tokyo (JP)

(72) Inventor: Brant Candelore, San Diego, CA (US)

(73) Assignee: SONY GROUP CORPORATION, Tokyo (JP)

( * ) Notice: Subject to any disclaimer, the term of this patent is extended or adjusted under 35 U.S.C. 154(b) by 739 days.

(21) Appl. No.: 17/307,372

(22) Filed: May 4, 2021

(65) Prior Publication Data

US 2022/0354978 A1 Nov. 10, 2022

(51) Int. Cl.
*A61L 2/10* (2006.01)
*A61L 2/24* (2006.01)

(52) U.S. Cl.
CPC .............. *A61L 2/24* (2013.01); *A61L 2/10* (2013.01); *A61L 2202/11* (2013.01); *A61L 2202/14* (2013.01)

(58) Field of Classification Search
CPC .......... A61L 2/10; A61L 2/24; A61L 2202/14; A61L 2202/11
USPC ................................................. 250/455.11
See application file for complete search history.

(56) References Cited

U.S. PATENT DOCUMENTS 6,730,923 B1 * 5/2004 May .................. A61L 2/10 426/240
2008/0265179 A1 10/2008 Havens et al.
2012/0056102 A1 3/2012 Stanley et al.
2018/0110890 A1 4/2018 Matsui

OTHER PUBLICATIONS

Chris Centeno, "Can a $99 UVC Wand From Amazon Provide COVID-Free Travel?", regenexx.com, May 19, 2020, 04 pages.
"3D Printer UV Resin Curing Light with Solar Turntable 360° Rotating Stand for SLA DLP LCD 3D Printer Solidify Photosensitive Resin 405nm UV Resin Affect, DIY Curing Enclosure", amazon.com, 2020, 04 pages.
"Rveal | UVILIZER Extra—UV Light Sanitizer & Portable Ultraviolet Sterilizer Wand (Rechargeable UV-C LED Disinfection Lamp | UVC Cleaner for Home, Car, Travel | Kills Germs, Bacteria, Viruses | USA)", amazon.com, 2020, 04 pages.

* cited by examiner

*Primary Examiner* — Kiet T Nguyen
(74) *Attorney, Agent, or Firm* — CHIP LAW GROUP

(57) ABSTRACT

An apparatus is provided for disinfection of an object. The apparatus includes a rotatable platform, a reflective surface on the rotatable platform, and a transmissive base to carry the object. The apparatus acquires information associated with the object, which includes one of a size of the object, a relative position, or an angular orientation of the object with respect to an ultraviolet light source. The apparatus determines one or more control parameters based on the acquired information, which includes one of a distance between the transmissive base and the reflective surface, a time period, or a speed of rotation of the rotatable platform. Based on the one or more control parameters, the apparatus controls a movement of the transmissive base and the rotation of the rotatable platform, to cause the reflective surface to reflect an ultraviolet light emitted by the ultraviolet light source onto the object, via the transmissive base.

13 Claims, 8 Drawing Sheets

APPARATUS AND METHOD FOR DISINFECTION OF OBJECT

CROSS-REFERENCE TO RELATED APPLICATIONS/INCORPORATION BY REFERENCES

None.

FIELD

Various embodiments of the disclosure relate to disinfection of an object. More specifically, various embodiments of the disclosure relate to an apparatus and method for disinfection of an object.

BACKGROUND

Everyday objects (such as packages, bags, grocery, or mail) may be generally picked up from one location and delivered to another location by a delivery partner (such as a courier). During transit, these objects may be handled by multiple delivery personnel and may come in contact with other objects being carried in containers. Due to such contact between the objects and the delivery personnel, pathogens (such as bacteria, virus, or other disease-causing germs) may be deposited on these objects. When these objects arrive at their final destination (such as homes or offices or other premises), users may pick up such objects with bare hands, and may subsequently touch their face without sanitizing or washing hands. This may put the users at risk of infection from such pathogens. There is an underlying fear of infection from handling such objects that enter the premises (such as homes or offices). Accordingly, it may be necessary to disinfect these everyday objects as soon as these objects enter the premises.

In some cases, an ultraviolet light source (such as sunlight or a handheld UV lamp) may be used to disinfect the objects by exposure to ultraviolet light from the ultraviolet light source, before the objects are used. However, the handheld UV lamp may be underpowered and may require a user to hold the handheld UV lamp for several minutes, which may make them impractical to use. Further, in case the ultraviolet light source (such as sunlight or a handheld UV lamp) is disposed at a fixed location, only a portion of the object (that may be exposed to the ultraviolet light) may be disinfected. However, other portions of the object (such as the underside of the object) may not be exposed to the ultraviolet light, and thus may not be properly disinfected. Therefore, conventional methods of disinfection of objects may be impractical or ineffective.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

An apparatus and method for disinfection of an object is provided substantially as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Figure 1:
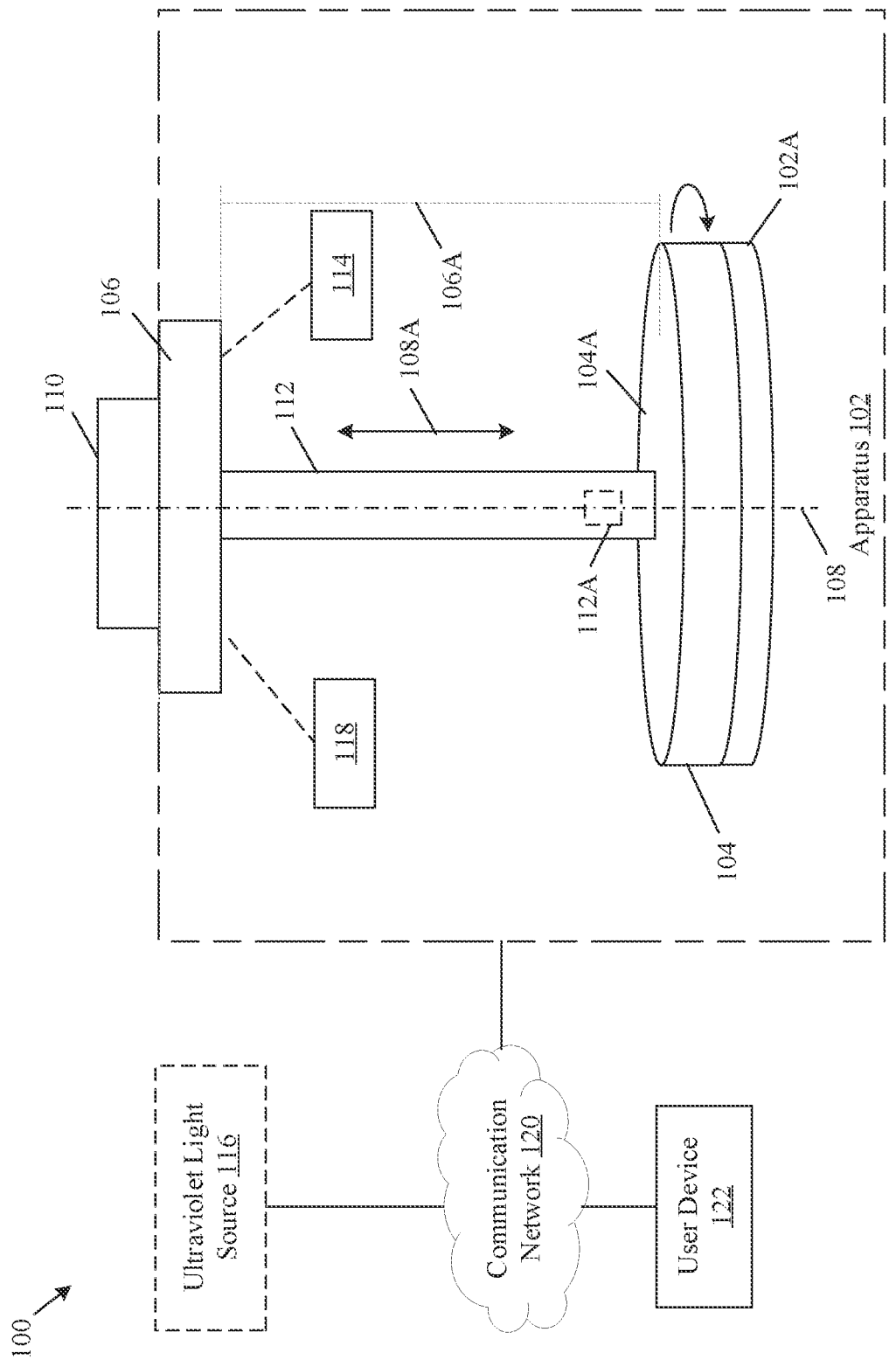
FIG. 1 is a block diagram that illustrates an exemplary network environment for disinfection of an object, in accordance with an embodiment of the disclosure.

The following described implementations may be found in a disclosed apparatus for disinfection of an object. Exemplary aspects of the disclosure provide an apparatus that may be configured to disinfect an object (such as a package, a bag, grocery, clothing, mail, money bills, etc.). The apparatus may include a rotatable platform configured to rotate about a first axis, a reflective surface on the rotatable platform, and a transmissive base that may be configured to carry an object. The transmissive base may be movable along a direction of the first axis. The transmissive base may be rotatably engaged with the rotatable platform through one or more connecting members. In an embodiment, the apparatus may be configured to acquire information associated with the object. For example, the information associated with the object may comprise a size of the object, a relative position of the object with respect to an ultraviolet light source (such as the sun or a portable ultraviolet lamp), or an angular orientation of the object with respect to the ultraviolet light source. Based on the acquired information, the apparatus may be configured to determine one or more control parameters. For example, the one or more control parameters may comprise at least one of a distance between the transmissive base and the reflective surface along the first axis, a time period of rotation of the rotatable platform, or a speed of the rotation of the rotatable platform. Based on the determined one or more control parameters (for example, the distance between the transmissive base and the reflective surface), the apparatus may control a movement of the transmissive base along the first axis. Based on the determined one or more control parameters (for example, the time period of rotation of the rotatable platform, or the speed of the rotation of the rotatable platform), the apparatus may control the rotation of the rotatable platform, to cause the reflective surface to reflect an ultraviolet light emitted by the ultraviolet light source onto the object, via the transmissive base. The rotation of the rotatable platform causes rotation of the transmissive base that may carry the object. Based on the rotation of the transmissive base, the ultraviolet light reflected onto the object via the transmissive base may disinfect all portions of the object.

The apparatus may control the rotatable platform to cause the reflective surface to reflect the ultraviolet light onto one or more portions (such as the underside) of the object, which may not be directly exposed to the ultraviolet light source, via the transmissive base, thereby effectively disinfecting all portions of the object. The apparatus may further change the distance between the transmissive base and the reflective surface based on one of the size of the object, a shape of the object, or a relative position of the object with respect to a fixed ultraviolet light source (such as the sun), to cause irradiation of the reflected ultraviolet light to all portions of the object. Details of the change in the distance between the transmissive base and the reflective surface, are further described, for example, in FIGS. 3A and 3B.

The apparatus may be further configured to determine the time period of the rotation of the rotatable platform, or the speed of the rotation of the rotatable platform based on a parameter (such as an intensity of the ultraviolet light or a wavelength of the ultraviolet light) associated with the ultraviolet light source. The apparatus may be configured to control the rotation of the rotatable platform, and thereby the rotation of the transmissive base that may carry the object, based on the determined time period of rotation, or the determined speed of the rotation of the rotatable platform. The rotation of the transmissive base may cause irradiation of the ultraviolet light onto different portions of the object for a required time period (such as several minutes), to thereby disinfect the object without manual effort. For example, in case the ultraviolet light source is disposed at a fixed location, the apparatus may control the rotation of the rotatable platform and the transmissive base to effectively disinfect all portions of the object. Details of the control of the rotation of the rotatable platform, are further described, for example, in FIGS. 3A and 5A.

In another embodiment, the apparatus may be configured to acquire an intensity of the ultraviolet light emitted by the ultraviolet light source from a sensor. The apparatus may further determine an emission time of the ultraviolet light from the ultraviolet light source based on at least one of the acquired intensity or a wavelength of the emitted ultraviolet light. The apparatus may control at least one of the time period of the rotation of the rotatable platform or the speed of the rotation of the rotatable platform based on the determined emission time, to thereby effectively disinfect the object under varying conditions of the ultraviolet light source (such as the sun or the portable ultraviolet lamp). For example, the apparatus may cause a timer to control the time period of the rotation of the rotatable platform based on an output (for example, measured intensity) of the sensor. Details of the timer for the control of the time period, are further described, for example, in FIG. 2.

In another embodiment, the reflective surface of the apparatus may have a concave surface. The concave surface of the reflective surface may be configured to reflect the ultraviolet light from the ultraviolet light source as a focused beam on the object. Such focused beam may facilitate the disinfection of a specific portion (such as a high touch point) of the object. Details of the focused beam for the disinfection, are further described, for example, in FIGS. 6A and 6B.

FIG. 1 is a block diagram that illustrates an exemplary network environment for disinfection of an object, in accordance with an embodiment of the disclosure. With reference to FIG. 1, there is shown a network environment 100. In the network environment 100, there is shown an apparatus 102. The apparatus 102 may include a rotatable platform 104 that may have a reflective surface 104A, and a transmissive base 106 that may be disposed at a distance 106A from the reflective surface 104A of the rotatable platform 104. The transmissive base 106 may be configured to carry an object 110. The transmissive base 106 may be rotatably engaged with the rotatable platform 104 through one or more connecting members 112. The transmissive base 106 may be movable along a direction of a first axis 108. The apparatus may further include an actuator 112A to control the movement of the transmissive base 106 and a rotation of the rotatable platform 104. The apparatus 102 may further include a first sensor 114 that may be configured to detect information associated with the object 110. The apparatus may further include a second sensor 118 that may be configured to measure a parameter (such as intensity or wavelength) associated with an ultraviolet light source 116. For example, the ultraviolet light source 116 may be a natural ultraviolet light source (such as the sun) or an artificial ultraviolet light source (such as a portable ultraviolet lamp). In case the ultraviolet light source 116 is an artificial ultraviolet light source, the apparatus 102 may be communicatively coupled with the ultraviolet light source 116 (such as a portable ultraviolet lamp) via a communication network 120. The apparatus 102 may be communicatively coupled with a user device 122.

The apparatus 102 may include suitable logic, circuitry, interfaces, and/or components that may be configured to disinfect the object 110 that may be carried by the transmissive base 106. For example, the apparatus 102 may acquire a parameter (such as intensity or wavelength) of the ultraviolet light emitted by the ultraviolet light source 116 from the first sensor 114. The apparatus 102 may acquire information (such as a size of the object 110, a relative position of the object 110 with respect to the ultraviolet light source 116, or an angular orientation of the object 110 with respect to the ultraviolet light source 116) associated with the object 110 from the second sensor 118. In an embodiment, the apparatus 102 may control the movement of the transmissive base 106 and the rotation of the rotatable platform 104 based on the information (such as the intensity of the ultraviolet light) acquired from the first sensor 114 and the second sensor 118. Based on the control, the apparatus 102 may cause the reflective surface 104A to reflect the ultraviolet light from the ultraviolet light source 116 onto the object 110 (for example, the underside of the object). Details of the irradiation and disinfection of the object 110 are further described, for example, in FIGS. 3A, 3B, 4, 5A, 5B, 6A, and 6B. In an embodiment, the apparatus 102 may include one or more rechargeable batteries that may supply power to different components of the apparatus 102. For example, the one or more rechargeable batteries may supply power for the rotation of the rotatable platform 102 and the movement of the transmissive base 106.

In an embodiment, the apparatus 102 may include a base 102A that may be disposed on a floor (not shown) of a premises (such as a home or an office) at a location that receives sunlight. The base 102A may be stationary and may be coupled to the rotatable platform 104 via a rolling-element bearing (such as ball bearings or rollers), so as to allow the rotation of the rotatable platform 104 with zero or minimal friction between the base 102A and the rotatable platform 104. The base 102A may made of a material with high tensile strength (such as metal or light-weight alloy) so as to bear the weight of the apparatus 102 and to maintain stability of the apparatus 102 during rotation of the rotatable platform 104 and the transmissive base 106.

The rotatable platform 104 may be configured to rotate the transmissive base 106 such that all portions of the object 110 carried by the transmissive base 106 may be exposed to the irradiation of the ultraviolet light source 116 (such as the sun) that may have a fixed position. In an embodiment, the apparatus 102 may control the rotation of the rotatable platform 104 to be one of a continuous rotation or a cyclic rotation. For example, the rotatable platform 104 may rest on the base 102A via a rolling-element bearing (such as ball bearings). The rotatable platform 104 may be configured to rotate about the first axis 108 to rotate the transmissive base 106 via the connecting members 112. Details of the rotation of the rotatable platform 104 are further described, for example, in FIGS. 3A, 3B, and 5A. In an embodiment, the rotatable platform 104 may have a substantially cylindrical profile. The substantially cylindrical profile of the rotatable platform 104 may provide stability to the apparatus 102 during the rotation of the rotatable platform 104. The substantially cylindrical profile of the rotatable platform 104 is presented merely as an example. In another example, the rotatable platform 104 may include a rectangular profile, or any other polygonal profile, without deviating from the scope of the disclosure. The description of such configurations of the rotatable platform 104 has been omitted from the disclosure for the sake of brevity. In an embodiment, the rotatable platform 104 may have the reflective surface 104A opposite to a surface that faces the base 102A.

The reflective surface 104A may be configured to reflect the irradiation that may be emitted from the ultraviolet light source 116 onto the transmissive base 106. For example, the reflective surface 104A may be made of a reflective material (such as, a mylar material, an acrylic mirror, or any material with reflective metal coating or dielectric material coating) that may be configured to reflect the radiation emitted from the ultraviolet light source 116. In an embodiment, the reflective surface 104A may be coaxially located on the rotatable platform 104 of the apparatus 102 to reflect the irradiation of the ultraviolet light source 116 towards the object 110. In an embodiment, the reflective surface 104A may be a part of a surface of the rotatable platform 104 that faces the transmissive base 106. Details of the reflection of the irradiation of the ultraviolet light source 116 are further described, for example, in FIGS. 3A, 3B, 4, 5A, 5B, 6A, and 6B.

In an embodiment, the reflective surface 104A may be a concave surface. The concavity of the reflective surface 104A may face the ultraviolet light source 116 and the transmissive base 106. In an example, the concavity of the reflective surface 104A may converge a portion of the ultraviolet light from the ultraviolet light source 116 as parallel rays onto the object 110. In another example, the concavity of the reflective surface 104A may converge a portion of the ultraviolet light from the ultraviolet light source 116, as a focused beam, onto the object 110. Details of the concave surface of the reflective surface 104A are described, for example, in FIGS. 6A and 6B. In another embodiment, the reflective surface 104A may be a planar surface, as shown in FIG. 1, that may spread rays of the ultraviolet light evenly onto the object 110. The planar surface of the reflective surface 104A, shown in FIG. 1, is presented merely as an example. In another example, the reflective surface 104A may include a convex surface, a textured surface, or a combination of planar and concave surfaces, without deviating from the scope of the disclosure. The description of such configurations of the reflective surface 104A has been omitted from the disclosure for the sake of brevity. In an embodiment, the reflective surface 104A and the transmissive base 106 may be coaxial with the rotatable platform 104. For example, the axis of rotation of the reflective surface 104A may be aligned with the first axis 108 about which the transmissive base 106 may rotate. The reflective surface 104A may be configured to reflect the ultraviolet light from the ultraviolet light source 116 (such as the sun or the portable ultraviolet lamp) towards the object 110, via the transmissive base 106.

Figure 3A:
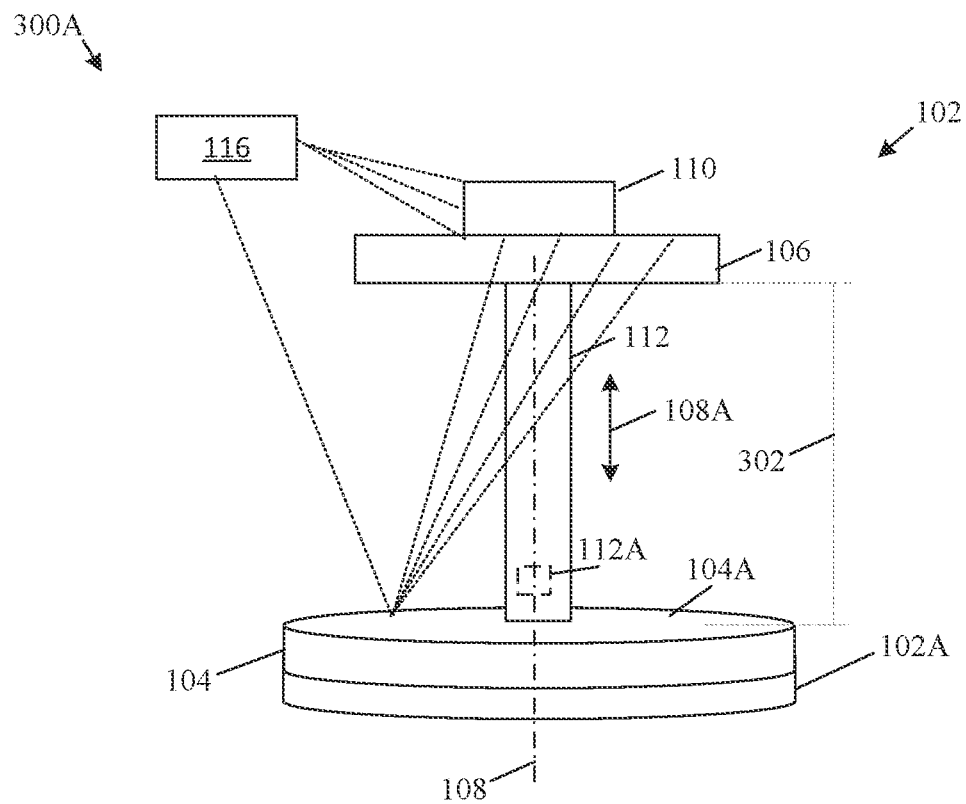
FIGS. 3A and 3B are diagrams that collectively illustrate an exemplary scenario for disinfection of an object, in accordance with an embodiment of the disclosure.
Figure 3B:
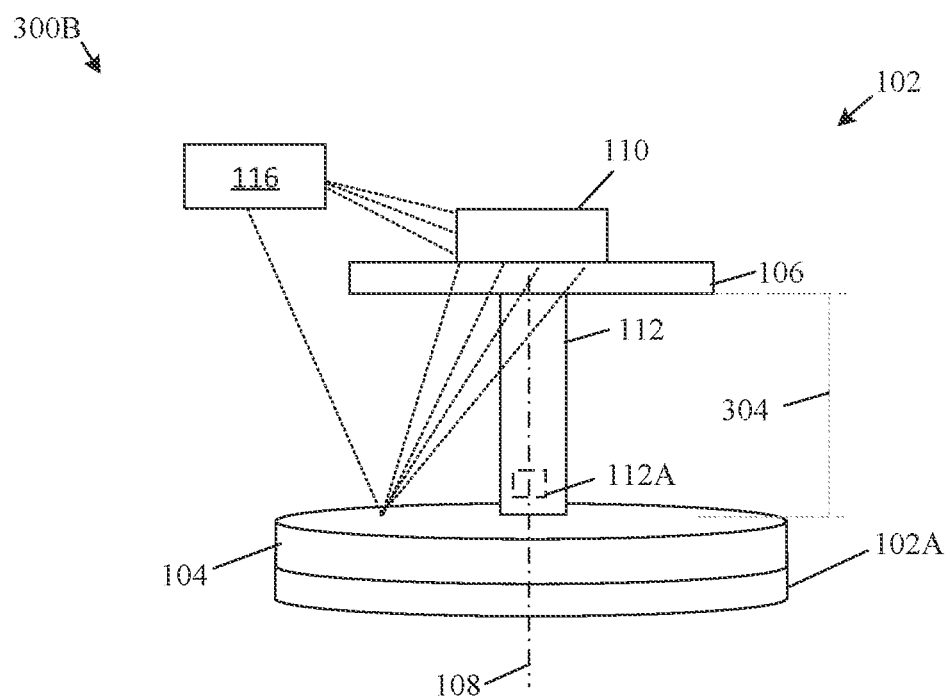

The transmissive base 106 may be configured to carry the object 110 on a surface opposite to a surface that faces the rotatable platform 104, as shown, for example, in FIGS. 3A and 3B. In an embodiment, the transmissive base 106 may carry the object 110 on the surface that faces the rotatable platform 104, as shown, for example, in FIGS. 5A and 5B. The transmissive base 106 may be configured to transmit the ultraviolet light reflected from the reflective surface 104A. For example, the transmissive base 106 may include an ultraviolet transmissive material (such as a polymer material, a glass material, or any material that is UV transmissive) that may be configured to transmit the reflected ultraviolet light from the surface of the transmissive base 106 that faces the rotatable platform 104 to the opposite surface of the transmissive base 106. In an embodiment, the transmissive base 106 may be rotatably engaged with the rotatable platform 104 via one or more connecting members 112. In an embodiment, the transmissive base 106 may be configured to rotate based on a coupling between the transmissive base 106 and the rotatable platform 104. For example, the transmissive base 106 may be configured to rotate with the rotation of the rotatable platform 104 at the same speed of rotation. In another embodiment, the transmissive base 106 may be rotatably engaged (such as via a gear train) with the rotatable platform 104, and the transmissive base 106 may relatively rotate based on the rotation of the rotatable platform 104. For example, the transmissive base 106 may rotate at a speed different from the speed of the rotation of the rotatable platform 104

In an embodiment, the transmissive base 106 may be movable along a direction 108A of the first axis 108. For example, based on the movement of the transmissive base 106 in the direction 108A of the first axis 108, the spread of the reflected ultraviolet light from the reflective surface 104A before the reflected ultraviolet light reaches the object 110 may be varied. Details of transmission of the reflection of the irradiation on the object 110 based on the movement of the transmissive base 106, are further described, for example, in FIGS. 3A and 3B. In another example, the transmissive base 106 may be rotatably engaged with the rotatable platform 104 through the connecting members 112. The rotation of the rotatable platform 104 may cause the rotation of the transmissive base 106, which in turn may cause the object 110 carried by the transmissive base 106 to rotate, to thereby cause different portions of the object 110 to be exposed to the ultraviolet light from the ultraviolet light source 116. The apparatus 102 may transmit the reflection of the irradiation from the ultraviolet light source 116 onto different portions of the object 110 based on the rotation of the object 110. Details of transmission of the reflected ultraviolet light onto the object 110 based on the rotation of the transmissive base 106, are further described, for example, in FIGS. 3A and 5A.

In an embodiment, the transmissive base 106 may have a substantially cylindrical profile. The substantially cylindrical profile of the transmissive base 106 may maintain a stability of the apparatus 102 during the rotation of the transmissive base 106 and may provide a large uniform surface area to stably carry the object 110. The cylindrical profile of the transmissive base 106 is presented merely as an example. In another example, the transmissive base 106 may include a rectangular profile, or any other polygonal profile, without deviating from the scope of the disclosure. The description of such configurations of the transmissive base 106 has been omitted from the disclosure for the sake of brevity.

Figure 5A:
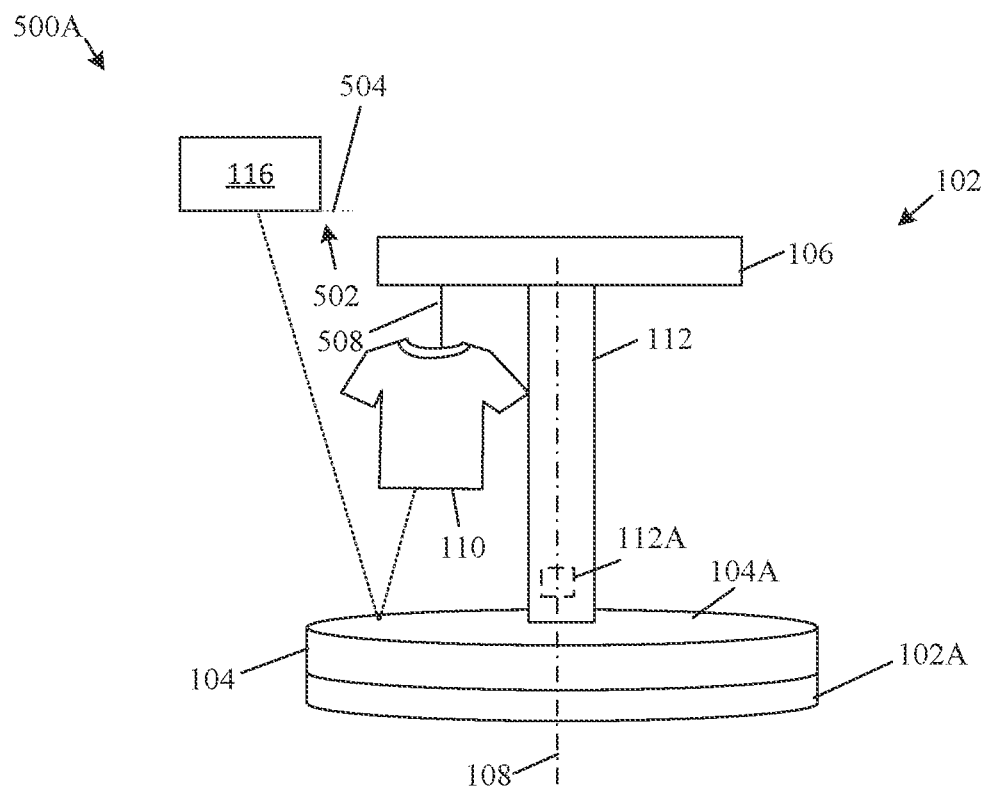
FIGS. 5A and 5B are diagrams that collectively illustrate an exemplary scenario for disinfection of an object, in accordance with an embodiment of the disclosure.
Figure 5B:
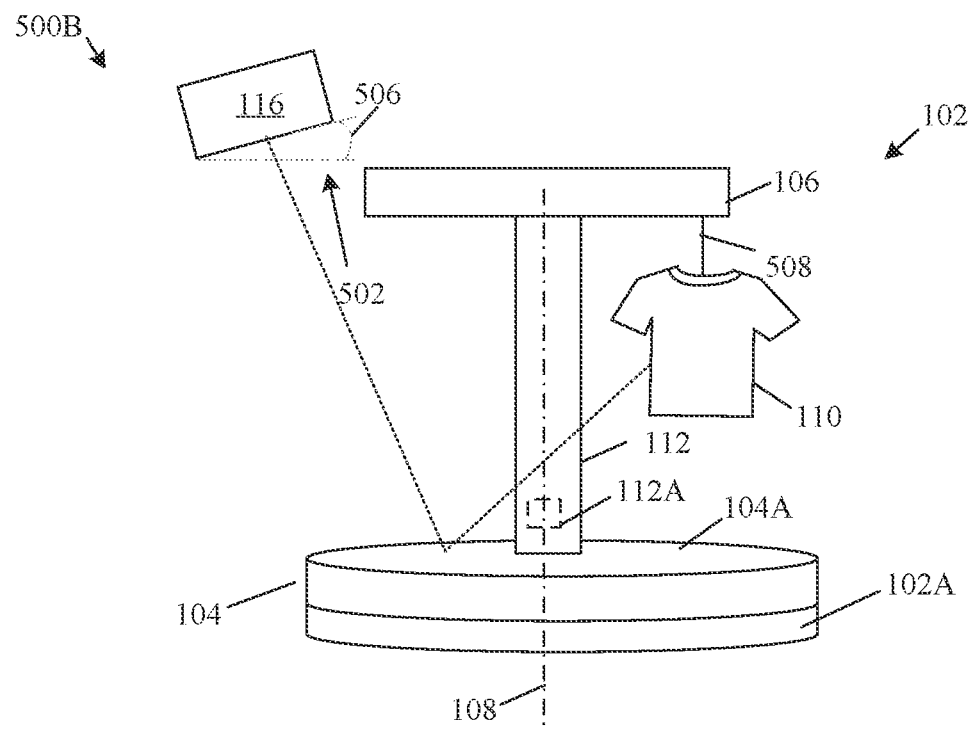

In an embodiment, the transmissive base 106 may include a planar surface to carry the object 110. In another example, the transmissive base 106 may include a chuck mechanism (not shown) that may be configured to firmly hold the object 110 during the rotation of the transmissive base 106 for disinfection of the object. In another embodiment, the transmissive base 106 may include a suspension element (such as a hanger or a hook) detachably attached to a surface of the transmissive base 106 that faces the rotatable platform 104. The transmissive base 106 may carry the object via the suspension element, as shown in FIGS. 5A and 5B.

The object 110 may be a tangible object (such as a package, a bag, clothing, grocery, mail, money bills, etc.) that may be carried by the transmissive base 106 for disinfection. In an embodiment, the orientation of the object 110 may be changed with respect to the irradiation from the ultraviolet light source 116 for disinfection, based on the rotation of the transmissive base 106. Details of the rotation of the object 110 with the respect to the ultraviolet light source 116 are further described, for example, in FIGS. 3A and 5A. In another embodiment, the object 110 may be moved with respect to reflective surface 104A for disinfection, based on the movement of the transmissive base 106. In an example, the movement of the object 110 may correspond to a change in an altitude of the object 110 with respect to the rotatable platform 104. In an embodiment, the movement of the object 110 with respect to the irradiation of the ultraviolet light source 116 may be controlled based on a movement of the connecting members 112. Details of the change in altitude of the object 110 by the movement of the transmissive base 106 are further described, for example, in FIGS. 3A and 3B. In an embodiment, the object 110 may include an inanimate object or a non-living entity. Examples of the object 110 may include, but are not limited to, a package, a pen, a device, a book, a mat, a carpet, a piece of clothing, a consumable item (such as a food item or a medicine), or any inanimate object that may be disposed on or carried by the transmissive base 106.

The connecting members 112 may be configured to couple the transmissive base 106 with the rotatable platform 104. In an example, the connecting members 112 may include a linkage mechanism (such as a mechanical linkage, a hydraulic linkage, a pneumatic linkage, or an electronic linkage) that may be configured to couple the transmissive base 106 with the rotatable platform 104. In an embodiment, the connecting members 112 may be disposed between the transmissive base 106 and the reflective surface 104A. In an example, the connecting members 112 may be disposed in an axis that may be parallel to the first axis 108 of rotation of the transmissive base 106. In another example, the connecting members 112 may be disposed in an axis that may be perpendicular to the first axis 108 of the rotation of the transmissive base 106. In an embodiment, the connecting members 112 may be configured to control the movement of the transmissive base 106 in the direction of the first axis 108. In an example, the connecting members 112 may control the translation of the transmissive base 106 to change the altitude of the object 110 with respect to the rotatable platform 104. Details of the control of the translation of the connecting members 112 are further described, for example, in FIGS. 3A and 3B. In another example, the connecting members 112 may control the rotation of the transmissive base 106 to control the rotation of the object 110 with respect to the irradiation from the ultraviolet light source 116. In an embodiment, the connecting members 112 may include a telescopic arrangement. The telescopic arrangement may include a first connecting member 112 (such as a hollow cylinder) that may be a telescopically engaged with a second connecting member 112 (such as a cylinder) such that a portion of the second connecting member 112 may move in and out of the first connecting member 112. The telescopic arrangement of the connecting members 112 is presented merely as an example. In another example, the connecting members 112 may include a rack and pinion configuration, a mechanical jack configuration, a hydraulic jack configuration, a pneumatic jack configuration, and the like, without deviating from the scope of the disclosure. The description of such configurations of the connecting members 112 has been omitted from the disclosure for the sake of brevity. In an embodiment, the movement of the connecting members 112 may controlled based on actuation from the actuator 112A.

The actuator 112A may be configured to control the rotation of the rotatable platform 104 and cause the rotation of the transmissive base 106, via the connecting members 112. For example, the actuator 112A may include a rotary actuator (such as a stepper motor) that may control the rotation of the rotatable platform 104 and further cause the rotation of the transmissive base 106, via the connecting members 112. In an embodiment, the actuator 112A may be disposed in at least one of the rotatable platform 104 or the connecting members 112. Details of the control of the actuator 112A are further described, for example, in FIGS. 3A, 3B, 6A, 6B, and 7. In an example, the actuator 112A may be a mechanical rotary actuator. The mechanical rotary actuator may include a geared mechanism that may include a rack and pinion arrangement to couple the transmissive base 106 with the rotatable platform 104. The mechanical rotary actuator is presented merely as an example. In another example, the actuator 112A may be any other form of rotatory actuator, which may include, but are not limited to, a pneumatic rotary actuator, a hydraulic rotary actuator, or an electronic rotary actuator. Other examples of the actuator 112A may include, but are not limited to, a servo motor, a linear motor, a stepper motor or other geared motors. Details of the actuator 112A are further described, for example, in FIGS. 5A and 5B.

In another embodiment, the actuator 112A may be further configured to control the movement of the transmissive base 106 in the direction 108A of the first axis 108, via the connecting members 112. For example, the actuator 112A may include a linear actuator for a double acting cylinder that may control the translation of the transmissive base 106, via the connecting members 112. In an embodiment, the actuator 112A may be disposed in at least one of the rotatable platform 104 or the connecting members 112. The actuator 112A may be configured to control the translation of the transmissive base 106, via the connecting members 112. Details of the control of the actuator 112A may be further described, for example, in FIGS. 3A and 3B. In an example, the actuator 112A may include an electro-mechanical linear actuator. The electro-mechanical linear actuator may control a double-acting cylinder that may have a piston arrangement or a telescopic arrangement coupled between the transmissive base 106 with the rotatable platform 104. Based on the movement of the piston arrangement of the electro-mechanical linear actuator, the apparatus 102 may control the movement between the transmissive base 106 and the reflective surface 104A of the rotatable platform 104. The electro-mechanical linear actuator is presented merely as an example. In another example, the actuator 112A may be any other form of linear actuator, which may include, but are not limited to, a pneumatic linear actuator, a hydraulic linear actuator, or a mechanical linear actuator.

The first sensor 114 may include suitable logic, circuitry, and interfaces that may be configured to capture an image or a plurality of images of the object 110 disposed on the transmissive base 106. Based on the captured images, the apparatus 102 may be further configured to acquire the information associated with the object 110. For example, the acquired information associated with the object 110 may include information related at least one of a size of the object 110, a relative position of the object 110 with respect to the ultraviolet light source 116, or an angular orientation of the object 110 with respect to the ultraviolet light source 116. In an embodiment, based on the acquired information of the object 110, the apparatus 102 may be further configured to control the one or more control parameters for at least one of the movement of the transmissive base 106, and/or the movement of the ultraviolet light source 116, to disinfect the object 110. Examples of the first sensor 114 may include, but are not limited to, an image sensor, a wide-angle camera, an action camera, a closed-circuit television (CCTV) camera, a camcorder, a digital camera, camera phones, a time-of-flight camera (ToF camera), a night-vision camera, a 360-degree camera, or other image capture devices. In an embodiment, the first sensor 114 (such as an image sensor) may be positioned near the transmissive base 106 to capture the image of the object 110 on the transmissive base 106. In another embodiment, the first sensor 114 (such as an image sensor) may be positioned near the ultraviolet light source 116 to capture the image of the object 110 on the transmissive base 106 from the viewpoint of the ultraviolet light source 116.

In another embodiment, the first sensor 114 may be a load sensor (such as a load cell) coupled to the transmissive base 106 to detect presence of the object 110 on the transmissive base 106. In another embodiment, the first sensor 114 may be an array of load sensors coupled to the transmissive base 106 to detect a size and weight of the object 110 on the transmissive base 106. In an embodiment, the first sensor 114 (such as the image sensor) may be remote from the apparatus 102, and may be connected to the apparatus 102 via the communication network 120. In another embodiment, the first sensor 114 (such as the load sensor) may be integrated with the apparatus 102. In another embodiment, the first sensor 114 may be communicatively coupled to the ultraviolet light source 116 (such as a portable ultraviolet lamp) and/or a timer (shown in FIG. 2) that may be configured to set the emission period of the ultraviolet light source 116 and the time period of rotation of the rotatable platform 104.

The ultraviolet light source 116 (such as an ultraviolet lamp) may include suitable logic, circuitry, and interfaces that may be configured to emit the ultraviolet light to disinfect the object 110. In an embodiment, the ultraviolet light source 116 may include a transceiver (such as a Wireless Fidelity (Wi-Fi) transceiver or a Bluetooth™ transceiver) for reception of control signals (such as ON or OFF signals) from the apparatus 102 via the communication network 120. For example, based on the relative position of the object 110 with respect to the ultraviolet light source 116, the apparatus 102 may control an intensity of the ultraviolet light source 116 emitted onto the object 110. In another example, based on the angular orientation of the object 110 with respect to the ultraviolet light source 116, the apparatus 102 may modify the wavelength (for example, in the range between 100 nm-400 nm) of the ultraviolet light emitted onto the object 110. Examples of the wavelength bands of the emitted ultraviolet light may include, but are not limited to, a UVA Band (for example, in the range between 315-400 nm), a UVB Band (for example, in the range between 280-315 nm), or a UVC Band (for example, in the range between 100-280 nm). Examples of the ultraviolet light source 116 may include, but are not limited to, a black light lamp, a short-wave UV lamp, an incandescent lamp, a gas-discharge lamp (such as a mercury-vapor lamp), an ultraviolet LED lamp, an ultraviolet laser, or a tunable vacuum ultraviolet.

In an embodiment, the ultraviolet light source 116 may be an ultraviolet lamp and may comprise one or more reflectors for control of one or more parameters (such as intensity, focus, directivity, or emission angle) of the emitted ultraviolet light. In an example, the ultraviolet lamp may be a floor lamp in the shape of a floodlight. In an embodiment, the ultraviolet light source 116 may comprise two or more UV lamps configured to emit ultraviolet light of the same wavelength or different wavelength ranges (such as UVA, UVB, and UVC bands). The apparatus 102 may further control the ultraviolet light source 116 to selectively activate a single UV lamp of the two or more UV lamps to emit the ultraviolet light of a specific wavelength range. In another embodiment, the apparatus 102 may further control the ultraviolet light source 116 to concurrently activate the two or more UV lamps to increase the power or the intensity of the emitted ultraviolet light. In some embodiments, the emission time of the ultraviolet light from the ultraviolet light source 116 may be synchronized with the time period of the rotation of the rotatable platform 104, such that the emission from the ultraviolet light source 116 and the rotation of the rotatable platform 104 may start and stop at the same time. In another embodiment, the emission time of the ultraviolet light from the ultraviolet light source 116 may be different from the time period of the rotation of the rotatable platform 104

The second sensor 118 may include suitable logic, circuitry, and interfaces that may be configured to measure a parameter (such as intensity or wavelength or any other ultraviolet index) of the ultraviolet light source 116. Based on the measured parameter, the apparatus 102 may be configured to acquire the information associated with the ultraviolet light source 116. For example, the acquired information associated with the ultraviolet light source 116 may include at least one of an intensity of the ultraviolet light source 116, a wavelength of the ultraviolet light source 116, or an emission angle of the ultraviolet light source 116. In an embodiment, based on the acquired information of the ultraviolet light source 116, the apparatus 102 may be further configured to control the one or more control parameters that may comprise a distance between the transmissive base 106 and the reflective surface 104A along the first axis 108, a time period of rotation of the rotatable platform 104, a speed of the rotation of the rotatable platform 104, or a movement of the ultraviolet light source 116 to disinfect the object 110. Examples of the second sensor 118 may include, but are not limited to, an image sensor, a photodiode, a photocathode, a spectrometer, a radiometer, a photomultiplier, or other measurement devices that may be sensitive to different parts of the UV spectrum. The second sensor 118 may be configured to measure the wavelength range (such as UVA, UVB, or UVC) of the ultraviolet light from the ultraviolet light source 116 (such as the sun or the portable ultraviolet lamp). The second sensor 118 may be configured to measure the intensity of the ultraviolet light from the ultraviolet light source 116 in terms of radiant flux (W/m$^2$) or other units. In an embodiment, the second sensor 118 may positioned near the transmissive base 106 such that the measured intensity corresponds to the intensity of the ultraviolet light incident on the object 110. In another embodiment, the second sensor 118 may positioned near the reflective surface 104A such that the measured intensity corresponds to the intensity of the ultraviolet light incident on the reflective surface 104A. In an embodiment, the second sensor 118 may be remote from the apparatus 102, and may be connected to the apparatus 102 via the communication network 120. In another embodiment, the second sensor 118 may be integrated with the apparatus 102. In an embodiment, the second sensor 118 may be communicatively coupled to the ultraviolet light source 116 (such as a portable ultraviolet lamp) and/or a timer (show in FIG. 2) that may be configured to set the emission period of the ultraviolet light source 116 and the time period of rotation of the rotatable platform 104.

The communication network 120 may include a communication medium through which the apparatus 102, and the ultraviolet light source 116, and the user device 122 may communicate with each other. The communication network 120 may be one of a wired connection or a wireless connection. Examples of the communication network 120 may include, but are not limited to, the Internet, a cloud network, a Wireless Fidelity (Wi-Fi) network, a Personal Area Network (PAN), a Local Area Network (LAN), or a Metropolitan Area Network (MAN). Various devices in the network environment 100 may be configured to connect to the communication network 120 in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity (Li-Fi), 802.16, IEEE 802.11s, IEEE 802.11g, multi-hop communication, wireless access point (AP), device to device communication, cellular communication protocols, and Bluetooth (BT) communication protocols. In an embodiment, the apparatus 102 may acquire information associated with the object 110 from the first sensor 114 via the communication network 120. In another embodiment, the apparatus 102 may acquire information associated with the ultraviolet light source 116 from the second sensor 118 via the communication network 120. The apparatus 102 may also receive control signals (such as ON/OFF signals for activation of the apparatus 102) from the user device 122 via the communication network 120. The apparatus 102 may transmit notifications (such as a disinfection completion notification) and other status messages to the user device 122 via the communication network 120. The apparatus 102 may transmit control signals to the ultraviolet light source 116 (such as portable ultraviolet lamp) via the communication network 120.

The user device 122 may include suitable logic, circuitry, and/or interfaces that may be configured to host an application associated with a graphical user interface for management of the disinfection of the object 110 by the apparatus 102. In some embodiments, the user device 122 may include the graphical user interface to receive one or more user inputs to remotely control the power supply (ON/OFF) of the apparatus 102 and the ultraviolet light source 116 (such as portable ultraviolet lamp), change the speed or the time period of rotation of the rotatable platform 104, change the emission time of the ultraviolet light source 116 (such as portable ultraviolet lamp), change the distance between the rotatable platform 104 and the transmissive base 106, or control other parameters (such as intensity or wavelength) of the ultraviolet light source 116 (such as the portable ultraviolet lamp) and the apparatus 102. The graphical user interface of the user device 122 may display notifications (for example, start notification and end notification of disinfection) and status messages (for example, time remaining for disinfection, error messages, etc.) received from the apparatus 102 based on a countdown of the timer (shown in FIG. 2). The user device 122 may also output an audio alert (such as a tone or synthesized speech) or a vibration-based alert for the notifications and the status messages. In another example, the user device 122 may receive a text message for notification of the completion of the disinfection. In an embodiment, the graphical user interface of the user device 122 may display a recommendation chart that indicates recommended time periods for disinfection of different types of the object 110 (such as clothing, paper-based objects, plastic-based objects, consumables, etc.). In another embodiment, the graphical user interface of the user device 122 may allow user input of the type and material of the object 110 from a dropdown menu, such that the apparatus 102 may automatically set the emission time (and/or the time period of the rotation of the rotatable platform 104), the intensity, or the wavelength of the ultraviolet light based on the user input. In an embodiment, the application may be downloaded to the user device 122 from a cloud server. Examples of the user device 122 may include, but are not limited to, a computing device, a smartphone, a cellular phone, a mobile phone, a tablet computer, and other portable devices.

In operation, the apparatus 102 may acquire the information associated with the object 110 from the first sensor 114. The information associated with the object 110 may include at least one of the size of the object 110, the relative position of the object 110 with respect to an ultraviolet light source 116, or the angular orientation of the object 110 with respect to the ultraviolet light source 116. The apparatus 102 may further determine one or more control parameters based on the acquired information associated with the object 110. The determined control parameters may include at least one of the distance 106A between the transmissive base 106 and the reflective surface 104A of the rotatable platform 104 along the first axis 108, the time period of rotation of the rotatable platform 104, or the speed of the rotation of the rotatable platform 104. The apparatus 102 may further control, based on the determined one or more control parameters, the movement of the transmissive base 106 along the direction 108A of the first axis 108 and/or the rotation of the rotatable platform 104, to cause the reflective surface 104A of the rotatable platform 104 to reflect the ultraviolet light emitted by the ultraviolet light source 116 onto the object 110, via the transmissive base 106.

The rotation of the rotatable platform 104 may cause the rotation of the transmissive base 106 that may carry the object 110. Based on the movement of the transmissive base 106 along the direction 108A of the first axis 108 and/or the rotation of the transmissive base 106, the apparatus 102 may cause both a direct ultraviolet light from the ultraviolet light source 116 and the reflected ultraviolet light from the reflective surface 104A to be irradiated onto different portions of the object 110, thereby causing exposure of all portions of the object 110 to the ultraviolet light, and effective disinfection of the object 110. The apparatus 102 may control the rotatable platform 104 to cause the reflective surface 104A to reflect the ultraviolet light onto one or more portions (such as the underside) of the object, which may not be directly exposed to the ultraviolet light source 116, via the transmissive base, thereby effectively disinfecting all portions of the object 110. In an embodiment, based on the movement of the transmissive base 106 in the direction 108A of the first axis 108, the spread of the reflected ultraviolet light from the reflective surface 104A before the reflected ultraviolet light reaches the object 110 may be varied (as shown in FIGS. 3A and 3B), thereby allowing the ultraviolet light to uniformly irradiate the object 110 of different sizes.

Figure 2:
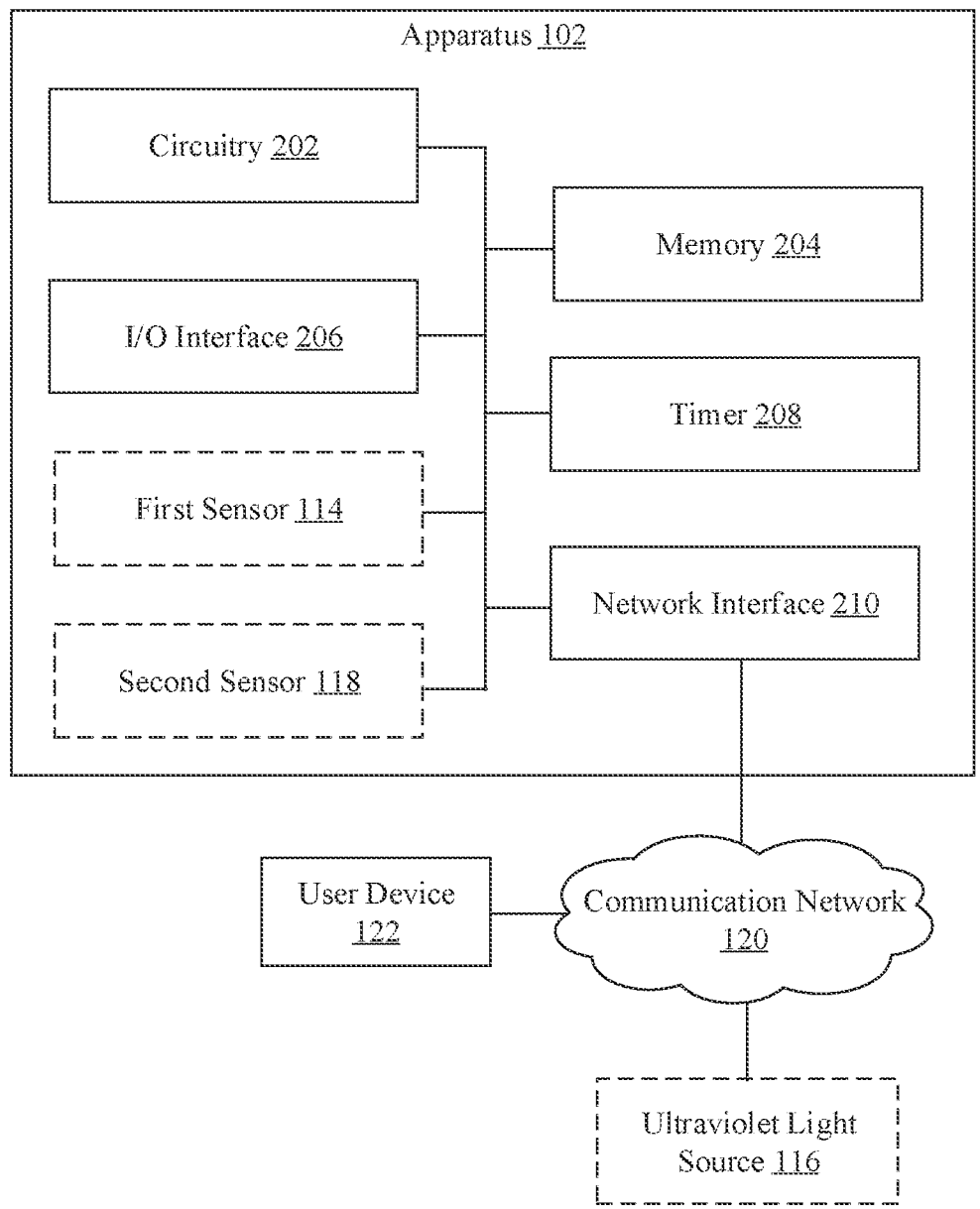
FIG. 2 is a block diagram that illustrates an exemplary architecture of an apparatus for disinfection of an object, in accordance with an embodiment of the disclosure.

FIG. 2 is a block diagram that illustrates an exemplary architecture of an apparatus for disinfection of an object, in accordance with an embodiment of the disclosure. FIG. 2 is explained in conjunction with elements from FIG. 1. With reference to FIG. 2, there is shown a block diagram 200 of the apparatus 102. The apparatus 102 may include circuitry 202, a memory 204, an I/O interface 206, a timer 208, and a network interface 210. In some embodiments, the apparatus 102 may include the first sensor 114 and the second sensor 118. In an embodiment, the apparatus 102 may be communicably coupled with the first sensor 114, the second sensor 118, the ultraviolet light source 116, and the user device 122, via a communication network 120.

The circuitry 202 may include suitable logic, circuitry, and/or interfaces that may be configured to execute program instructions associated with different operations to be executed by the apparatus 102. For example, some of the operations may include, but are not limited to, acquisition of information associated with the object 110, determination of the one or more control parameters (such as the distance 106A between the transmissive base 106 and the reflective surface 104A along the first axis 108, the time period of rotation of the rotatable platform 104) based on the acquired information associated with the object 110, and control of the movement of the transmissive base 106 along the direction 108A of the first axis 108 and/or the rotation of the rotatable platform 104. Based on the movement of the transmissive base 106 along the direction 108A of the first axis 108 and/or the rotation of the rotatable platform 104, the circuitry 202 causes the ultraviolet light from the ultraviolet light source 116 to be irradiated onto all parts of the object 110. The execution of operations may be further described, in FIGS. 3A, 3B, 4, 5A, 5B, 6A, and 6B.

The circuitry 202 may include any suitable special-purpose or general-purpose computer, computing entity, or processing device including various computer hardware or software modules and may be configured to execute instructions stored on any applicable computer-readable storage media (for example, the memory 204). The circuitry 202 may be implemented based on several processor technologies known in the art. For example, the circuitry 202 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data. The circuitry 202 may include any number of processors configured to, individually or collectively, perform any number of operations of the apparatus 102, as described in the present disclosure. Examples of the circuitry 202 may include a Central Processing Unit (CPU), a Graphical Processing Unit (GPU), an x86-based processor, an x64-based processor, a Reduced Instruction Set Computing (RISC) processor, a Complex Instruction Set Computing (CISC) processor, and/or other hardware processors. In an embodiment, the circuitry 202 may be configured to store, in the memory 204, information associated with the object 110, information associated with the ultraviolet light source 116, and information associated with the one or more control parameters for the disinfection of the object 110, The memory 204 may include suitable logic, circuitry, interfaces, and/or code that may be configured to store the set of instructions executable by the circuitry 202. In an embodiment, the memory 204 may be configured to store the information associated with the ultraviolet light source 116. The memory 204 may be further configured to store information associated with the object 110 disposed on the apparatus 102. The memory 204 may be further configured to store information associated with the one or more control parameters for the disinfection of the object 110. In an embodiment, the memory 204 may store a recommendation chart that indicates recommended time periods for disinfection of different types of the object 110 (such as clothing, paper-based objects, plastic-based objects, consumables, etc.). In another embodiment, the memory 204 may store first association information that associates the type or material of the object 110 with the emission time, the intensity, or the wavelength of the ultraviolet light. For example, the memory 204 may store a first emission time (such as twenty minutes) in association with a first type of object (such as clothing) and may store a second emission time (such as ten minutes) in association with a second type of object (such as paper-based objects). The circuitry 202 may utilize the first association information to automatically set the emission time, intensity, or wavelength of the ultraviolet light based on the type of the object 110 detected by the first sensor 114, or based on user input for the type of the object 110.

In another embodiment, the memory 204 may store second association information that associates intensity or wavelength of the ultraviolet light with the emission time of the ultraviolet light. For example, the memory 204 may store a first emission time (such as twenty minutes) in association with a first wavelength (such as UVA or UVB) and may store a second emission time (such as five minutes) in association with a second wavelength (such as UVC). The circuitry 202 may utilize the second association information to automatically set the emission time of the ultraviolet light based on the intensity or wavelength of the ultraviolet light detected by the second sensor 118. In another embodiment, the memory 204 may store history information related to emission time or intensity of the ultraviolet light for a specific type of the object 110, such that the circuitry 202 may set the emission time or the intensity of the ultraviolet light in case a similar type of object 110 is detected by the first sensor 114. Examples of implementation of the memory 204 may include, but are not limited to, Random Access Memory (RAM), Read Only Memory (ROM), Hard Disk Drive (HDD), a Solid-State Drive (SSD), a CPU cache, and/or a Secure Digital (SD) card.

The I/O interface 206 may include suitable logic, circuitry, interfaces, and/or code that may be configured to receive one or more user inputs and may render output (such as the notifications) in response to the received user inputs. In an embodiment, the I/O interface 206 may be integrally coupled to the apparatus 102 to receive the user inputs. For example, the I/O interface 206 may include a touchscreen display capable of receiving touch input that allows user input such as the emission time and the type of the object 110, and may display status messages (such as time remaining for completion of the disinfection) or warning messages (such as "UV emission in progress, please stay away"). In some embodiments, the I/O interface 206 may include various input and output devices, that may be configured to communicate with the circuitry 202. Examples of such input and output devices may include, but are not limited to, a touchscreen, a keyboard, a mouse, a joystick, a microphone, an image sensor, a display device, a speaker, and/or a vibration actuator.

The timer 208 may include suitable logic, circuitry, interfaces, and/or code that may be configured to set a countdown timer for the determined time period of the rotation of the rotatable platform 104 and/or the determined emission time of the ultraviolet light from the ultraviolet light source 116. In an example, the timer 208 may include a digital counter or clock that may countdown the time period of the rotation of the rotatable platform 104, based on the information detected by the first sensor 114 and the second sensor 118. Based on the start of the timer 208, the circuitry 202 may control the rotation of the rotatable platform 104, to cause the reflective surface 104A to reflect the ultraviolet light emitted by the ultraviolet light source 116 onto the object 110, via the transmissive base 106. Based on the expiry of the time period set in the timer 208, the circuitry 202 may stop the rotation of the rotatable platform 104 and/or the emission of the ultraviolet light from the ultraviolet light source 116, concurrently. Examples of the timer 208 may include, but are not limited to, a software timer, a digital clock, or an internal clock associated with the apparatus 102. In an embodiment, the timer 208 may be configured to set a first countdown timer to countdown the emission time of the ultraviolet light emitted by the ultraviolet light source 116. The timer 208 may be configured to set a second countdown timer, different from the first time period, to countdown the time period of the rotation of the rotatable platform 104. The circuitry 202 may start and stop the rotation of the rotatable platform 104 based on the first countdown timer (such as ten minutes), and may start and stop the emission of the ultraviolet light emitted by the ultraviolet light source 116 based on the second countdown timer (such as eleven minutes). In another embodiment, the timer 208 may be configured to synchronize the start and stop timings of the emission time of the ultraviolet light by the ultraviolet light source 116 with the rotation of the rotatable platform 104.

The network interface 210 may include suitable logic, circuitry, and interfaces that may be configured to facilitate communication between the circuitry 202 and the first sensor 114, the second sensor 118, the user device 122, or the ultraviolet light source 116 via the communication network 120. The network interface 210 may be implemented by use of various known technologies to support wired or wireless communication of the apparatus 102 with the communication network 120. Examples of the network interface 210 may include, but are not limited to, an antenna, a radio frequency (RF) transceiver, one or more amplifiers, a tuner, one or more oscillators, a digital signal processor, a coder-decoder (CODEC) chipset, a subscriber identity module (SIM) card, a Radio-Frequency Identification Device (RFID), a Bluetooth® Transceiver, or a local buffer circuitry. The network interface 210 may be configured to communicate via wireless communication with networks, such as the Internet, an Intranet or a wireless network, such as a cellular telephone network, a wireless local area network (LAN), and a metropolitan area network (MAN). The wireless communication may be configured to use one or more of a plurality of communication standards, protocols and technologies, such as Global System for Mobile Communications (GSM), Enhanced Data GSM Environment (EDGE), wideband code division multiple access (W-CDMA), Long Term Evolution (LTE), code division multiple access (CDMA), time division multiple access (TDMA), Bluetooth, Wireless Fidelity (Wi-Fi) (such as IEEE 802.11a, IEEE 802.11b, IEEE 802.11g or IEEE 802.11n), voice over Internet Protocol (VoIP), light fidelity (Li-Fi), Worldwide Interoperability for Microwave Access (Wi-MAX), a protocol for email, instant messaging, and a Short Message Service (SMS), via the communication network 120.

Although FIG. 2 illustrates the apparatus 102 includes the circuitry 202, the memory 204, the I/O interface 206, the timer 208, and the network interface 210, the disclosure may not be limited in this regard. Accordingly, the apparatus 102 may include more or less components to perform the same or other functions of the apparatus 102. Details of the other functions and the components have been omitted from the disclosure for the sake of brevity. The functions or operations executed by the apparatus 102, as described in FIG. 1, may be performed by the circuitry 202. Operations executed by the circuitry 202 are described, for example, in FIGS. 3A, 3B, 4, 5A, 5B, 6A, 6A, and 7.

FIG. 3A is a diagram that illustrates an exemplary scenario for disinfection of an object, in accordance with an embodiment of the disclosure. FIG. 3A is explained in conjunction with elements from FIGS. 1 and 2. With reference to FIG. 3A, there is shown an exemplary scenario 300A.

In the exemplary scenario 300A, the transmissive base 106 may be disposed at a first distance 302 from the reflective surface 104A of the rotatable platform 104. As seen in FIG. 3A, the reflection of the ultraviolet light from the reflective surface 104A may not uniformly irradiate the underside of the object 110, and a portion of the reflected ultraviolet light may not be incident on the object 110. Further, the intensity of the reflected ultraviolet light may deteriorate in case the object 110 is at a greater distance from the reflective surface 104A. In such a case, the ultraviolet light may not effectively disinfect the object 110. In order to effectively disinfect the object 110, the circuitry 202 may be configured to change a distance (such as the first distance 302) between the transmissive base 106 and the reflective surface 104A along the first axis 108, based on the movement of the transmissive base 106. For example, the circuitry 202 may be configured to control the actuator 112A to control the movement of the transmissive base 106, via the connecting members 112.

FIG. 3B is a diagram that illustrates an exemplary scenario for disinfection of an object, in accordance with an embodiment of the disclosure. FIG. 3B is explained in conjunction with elements from FIGS. 1, 2, and 3A. With reference to FIG. 3B, there is shown an exemplary scenario 300B.

In the exemplary scenario 300B, the circuitry 202 may control the actuator 112A to change the distance between the transmissive base 106 and the reflective surface 104A of the rotatable platform 104, via the connecting members 112. For example, the actuator 112A may control a first connecting member 112 that may be a telescopically engaged with a second connecting member 112 to change the distance between the transmissive base 106 and the rotatable platform 104. Based on the acquired information associated with at least one of the object 110 or the ultraviolet light source 116, the circuitry 202 may control the actuator 112A to modify (for example, reduce) the first distance 302 to a second distance 304, so as to uniformly irradiate the ultraviolet light at a higher intensity onto the object 110, and thereby effectively disinfect the object 110. In an example, the second distance 304 may be less than the first distance 302 in case the size of the object is smaller. In another example, the second distance 304 may be greater than the first distance 302 in case the size of the object is larger. The circuitry 202 may modify the first distance 302 to the second distance 304, to control the spread of the reflected ultraviolet light rays before the reflected ultraviolet light reaches the object 110, such that, the object 110 may be uniformly irradiated with the reflected ultraviolet light. As seen in FIG. 3B, a greater amount of the reflected ultraviolet light may be incident on the object 110, compared to the exemplary scenario 300A. The circuitry 202 may also change the first distance 302 based on the measured intensity of the ultraviolet light by the second sensor 118. For example, the circuitry 202 may reduce the first distance 302 in case the measured intensity of the ultraviolet light from the ultraviolet light source 116 is lower than a threshold.

Figure 4:
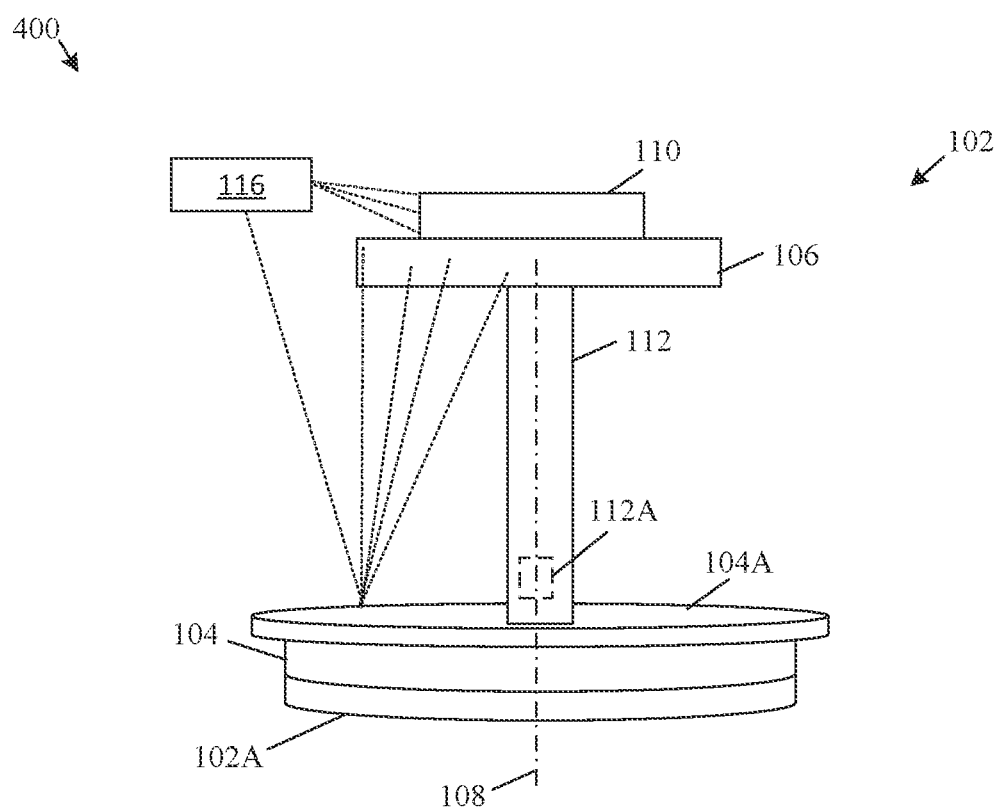
FIG. 4 is a diagram that illustrates an exemplary scenario for disinfection of an object, in accordance with an embodiment of the disclosure.

FIG. 4 is a diagram that illustrates an exemplary scenario for disinfection of an object, in accordance with an embodiment of the disclosure. FIG. 4 is explained in conjunction with elements from FIGS. 1, 2, 3A, and 3B. With reference to FIG. 4, there is shown an exemplary scenario 400.

In the exemplary scenario 400, the reflective surface 104A may be separate from the rotatable platform 104. As shown in FIG. 4, the reflective surface 104A may be wider in surface area than the rotatable platform 104. The wider surface area of the reflective surface 104A may cause a greater amount of the ultraviolet light from the ultraviolet light source 116 to be reflected onto the object 110 via the transmissive base 106. The reflective surface 104A may be made of a light-weight material compared to the rotatable platform 104, and may reduce the overall weight of the apparatus 102 while providing a wider surface area for the reflection of the ultraviolet light from the ultraviolet light source 116. In the exemplary scenario 400, the transmissive base 106 may be detachably attached to the connecting members 112, and the rotatable platform 104 may be detachably attached to the connecting members 112. The reflective surface 104A may be removably engaged with the rotatable platform 104 and/or the connecting members. In such a case, the apparatus 102 may be assembled for use to disinfect the object 110, and may be disassembled for storage when not in use.

FIG. 5A is a diagram that illustrates an exemplary scenario for disinfection of an object, in accordance with an embodiment of the disclosure. FIG. 5A is explained in conjunction with elements from FIGS. 1, 2, 3A, 3B, 4. With reference to FIG. 5A, there is shown an exemplary scenario 500A.

In the exemplary scenario 500A, the circuitry 202 may acquire the information associated with the ultraviolet light source 116 from the second sensor 118. The information associated with the ultraviolet light source 116 may include at least one of the location of the ultraviolet light source 116, the angular orientation of the ultraviolet light source 116 with respect to the reflective surface 104A, the wavelength of the ultraviolet light from the ultraviolet light source 116. Based on the acquired information associated with the ultraviolet light source 116, the circuitry 202 may determine one or more control parameters to control at least one of the rotation of the rotatable platform (as described in FIG. 5A), or the inclination of the ultraviolet light source 116 (as described in FIG. 5B).

In an embodiment, the circuitry 202 may acquire the measured intensity of the ultraviolet light from the second sensor 118. Based on the measured intensity of the ultraviolet light, the circuitry 202 may control at least one of the time period (for example, in the range of 10-20 minutes) of the rotation of the rotatable platform 104 or the speed (for example, in the range of 1-10 rotations per minute (RPM)) of the rotation of the rotatable platform 104. In another embodiment, the circuitry 202 may determine the emission time of the ultraviolet light from the ultraviolet light source 116 based on at least one of the acquired intensity or the wavelength of the emitted ultraviolet light. Based on the determined emission time, the circuitry 202 may be configured to control at least one of the time period of the rotation of the rotatable platform 104 or the speed of the rotation of the rotatable platform 104, to disinfect all portions of the object 110. The circuitry 202 may also vary the speed of the rotation of the rotatable platform 104 based on a change in the intensity of the ultraviolet light from the ultraviolet light source 116 (such as the sun) in the same disinfection cycle. The circuitry 202 may also control the rotation of the rotatable platform 104 to be a continuous rotation or a cyclic rotation, based on a change in the intensity of the ultraviolet light from the ultraviolet light source 116 (such as the sun), or based on the texture, shape, and size of the object 110. For example, the circuitry 202 may cause the rotatable platform 104 to rotate at ten RPM for two minutes, and then cause the rotatable platform 104 to be stationary for 30 seconds, and thereafter continue the rotation of the rotatable platform 104 for another two minutes, and so on.

In an embodiment, the object 110 (such as clothing) may be suspended from the lower surface of the transmissive base 106, as shown in FIG. 5A. For example, the transmissive base 106 may include a detachable suspension element 508 (such as a hangar or a hook) detachably attached to the surface of the transmissive base 106 that faces the reflective surface 104A. The object 110 may be suspended from the transmissive base 106 by the detachable suspension element 508. Based on the rotation of the rotatable platform 104, the object 110 may be disposed at a first side (for example, a left side) of the apparatus 102 at a first time instant. As shown in FIG. 5B, the object 110 may be disposed at a second side (for example, a right side) of the apparatus 102 at a second time instant, based on the rotation of the rotatable platform 104. Based on a position 502 and a first angular orientation 504 of the ultraviolet light source 116 shown in the exemplary scenario 500A, a large amount of the ultraviolet light may not be reflected onto the object 110 via the reflective surface 104A at the second time instant.

FIG. 5B is a diagram that illustrates an exemplary scenario for disinfection of an object, in accordance with an embodiment of the disclosure. FIG. 5B is explained in conjunction with elements from FIGS. 1, 2, 3A, 3B, 4, and 5A. With reference to FIG. 5B, there is shown an exemplary scenario 500B. In the exemplary scenario 500B, the circuitry 202 may control the orientation of the ultraviolet light source 116 to disinfect the object 110. As shown in FIG. 5B, the object 110 may be disposed at a second side (for example, a right side) of the apparatus 102 at the second time instant, based on the rotation of the rotatable platform 104.

In an embodiment, the circuitry 202 may be further configured to transmit a control signal to the ultraviolet light source 116 based on the determined one or more control parameters. The control signal may be configured to control a parameter associated with the ultraviolet light source 116. In an embodiment, the parameter may include at least one of the emission time of the ultraviolet light emitted by the ultraviolet light source 116, the angular orientation of the emitted ultraviolet light, the wavelength of the emitted ultraviolet light, or the intensity of the emitted ultraviolet light. In an embodiment, in case the first sensor 114 detects that the ultraviolet light source 116 may not irradiate the object 110 based on the position of the object 110 at the second time instant, the circuitry 202 may change the angular orientation of the ultraviolet light source 116. For example, the circuitry 202 may transmit the control signal to change the first angular orientation 504 of the ultraviolet light source 116 to a second angular orientation 506 (as shown in FIG. 5B) at the second time instant. Based on the second angular orientation 506 of the ultraviolet light source 116, the circuitry 202 may effectively irradiate the reflected ultraviolet light onto the object 110 and cause the disinfection of the object 110. In an embodiment, the circuitry 202 may change the second angular orientation 506 of the ultraviolet light source 116 back to the first angular orientation 504 at a third time instant, as the position of the object 110 changes based on the rotation of the rotatable platform 104. The circuitry 202 may continuously change the angular orientation of the ultraviolet light source 116 between the first angular orientation 504 and the second angular orientation 506 till the rotation of the rotatable platform 104 has stopped. In another embodiment, the circuitry 202 may alternatively control (for example, increase) the intensity of the ultraviolet light source 116, such that the object 110 is irradiated with high intensity ultraviolet light irrespective of the position of the object 110.

Figure 6A:
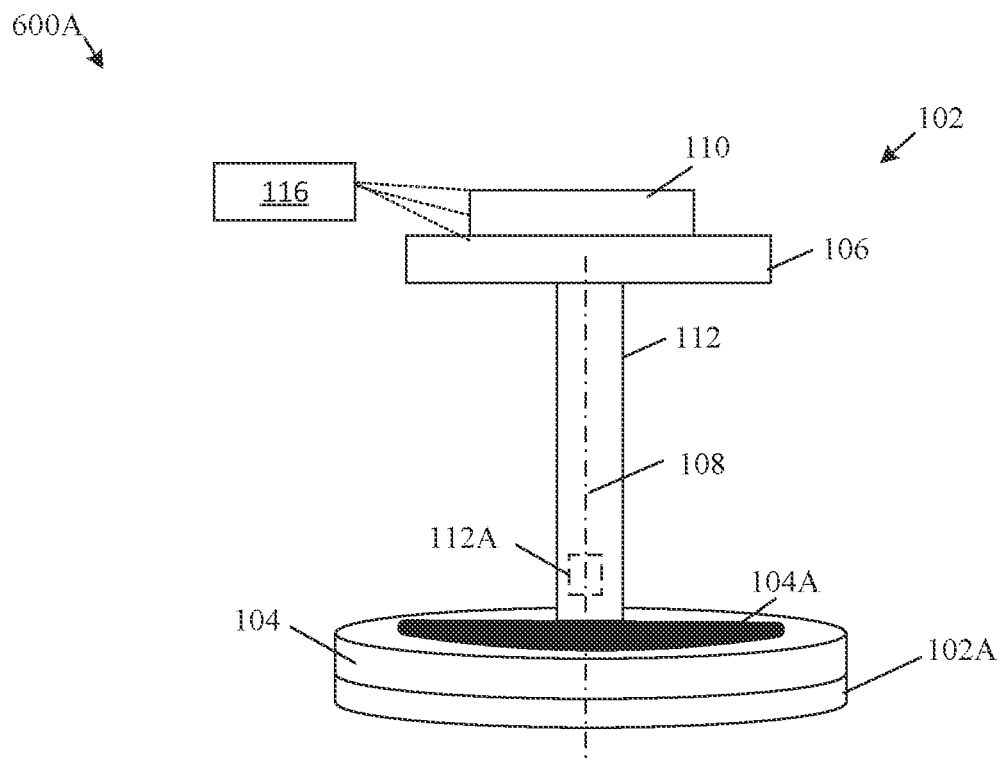
FIGS. 6A and 6B are diagrams that collectively illustrate an exemplary scenario for disinfection of an object, in accordance with an embodiment of the disclosure.

FIG. 6A is a diagram that illustrates an exemplary scenario to disinfect an object, in accordance with an embodiment of the disclosure. FIG. 6A is explained in conjunction with elements from FIGS. 1, 2, 3A, 3B, 4, 5A, and 5B. With reference to FIG. 6A, there is shown an exemplary scenario 600A. In the exemplary scenario 600A, the reflective surface 104A may have a concave surface. The concavity of the reflective surface 104A may face the ultraviolet light source 116 and the transmissive base 106. In an example, the concavity of the reflective surface 104A may converge a portion of the ultraviolet light from the ultraviolet light source 116 as parallel rays onto the object 110. In another example, the concavity of the reflective surface 104A may converge a portion of the ultraviolet light from the ultraviolet light source 116, as a focused beam, onto the object 110, as described, for example, in FIG. 6B.

Figure 6B:
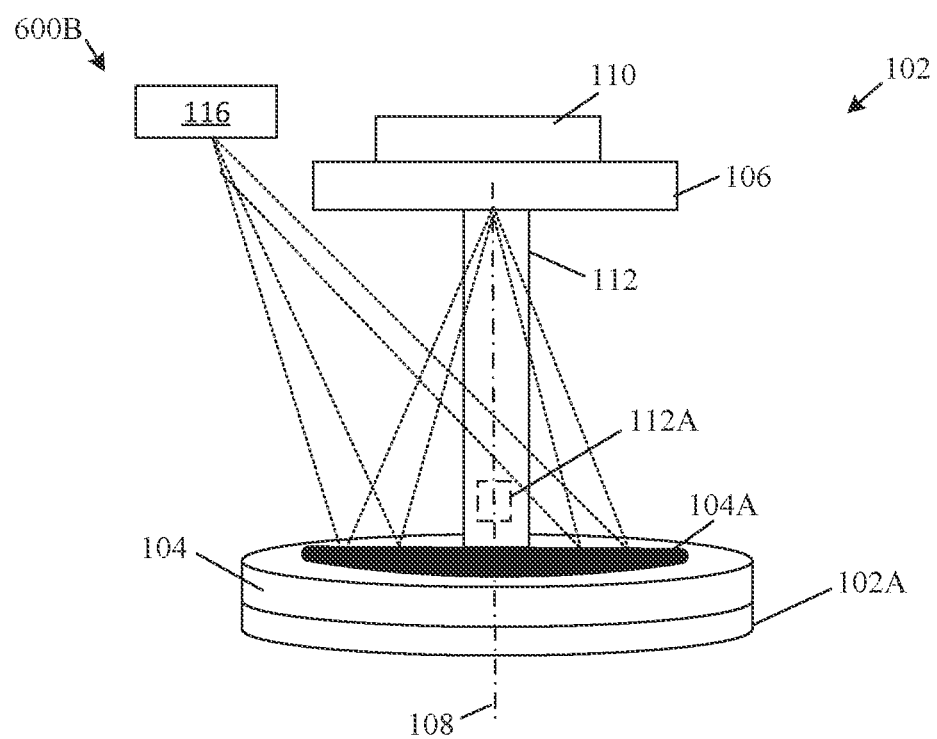

FIG. 6B is a diagram that illustrates an exemplary scenario to disinfect an object, in accordance with an embodiment of the disclosure. FIG. 6B is explained in conjunction with elements from FIGS. 1, 2, 3A, 3B, 4, 5A, 5B, and 6A. With reference to FIG. 6B, there is shown an exemplary scenario 600B. In the exemplary scenario 600B, based on the irradiation from the ultraviolet light source 116, the reflective surface 104A may converge a portion of the ultraviolet light from the ultraviolet light source 116 as a focused beam onto the object 110, via the transmissive base 106. The focused beam of the ultraviolet light may cause disinfection of a specific portion (such as a high touch point) of the object 110 with high-intensity ultraviolet light.

Figure 7:
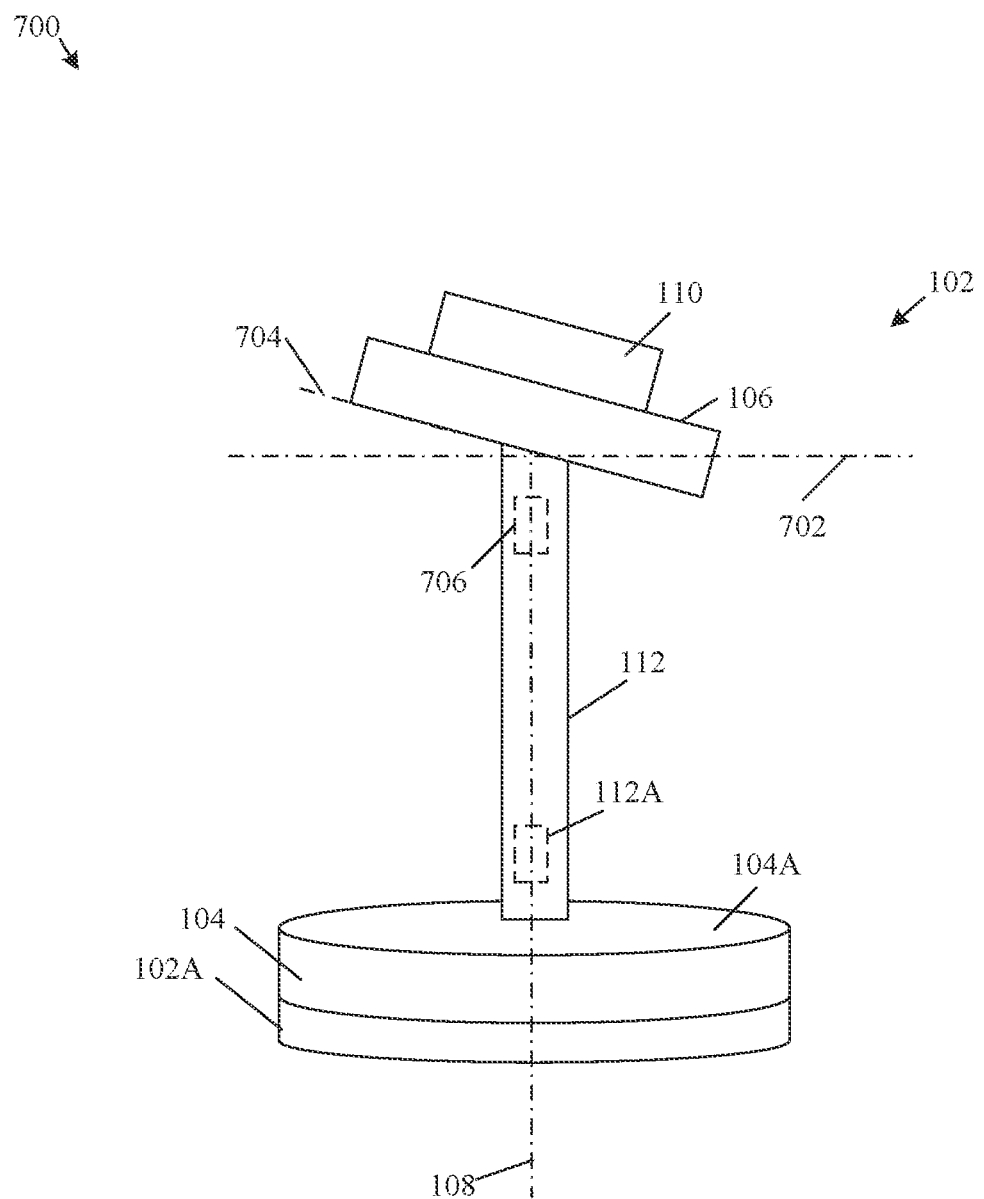
FIG. 7 is a diagram that illustrates an exemplary scenario for disinfection of an object, in accordance with an embodiment of the disclosure.

FIG. 7 is a diagram that illustrates an exemplary scenario for disinfection of an object, in accordance with an embodiment of the disclosure. FIG. 7 is explained in conjunction with elements from FIGS. 1, 2, 3A, 3B, 4, 5A, 5B, 6A, and 6B. With reference to FIG. 7, there is shown an exemplary scenario 700.

In the exemplary scenario 700, there is shown a disinfected object 110 on the transmissive base 106. For example, the circuitry 202 may cause the ultraviolet light from ultraviolet light source 116 to disinfect the object 110 to provide the disinfected object 110. The structural and functional features of the disinfected object 110 is same as the object 110, shown in FIG. 1. Accordingly, a description of the disinfected object 110 has been omitted for the sake of brevity. Based on completion of the disinfection, the circuitry 202 may control an actuator 706 to pivot or tilt the transmissive base 106 about a second axis 702 to be parallel with a third axis 704. The tilt of the transmissive base 106 may allow for easy access to the object 110 by a user. In another example, the circuitry 202 may control the actuator 706 to tilt the transmissive base 106 about the second axis 702 based on user input via the I/O interface shown in FIG. 2. In another example, the circuitry 202 may control the actuator 706 to pivot the transmissive base 106 about the second axis 702 based on the position of the ultraviolet light source 116 (such as the sun). In another embodiment, the apparatus 102 may be a part of an automated assembly line, and may be configured to disinfect the object 110 (such as an assembled product or a package) on the assembly line. Based on the completion of the disinfection, the circuitry 202 may cause the transmissive base 106 to tilt by a certain angle, such that the disinfected object 110 may slide off to a subsequent belt in the assembly line.

Figure 8:
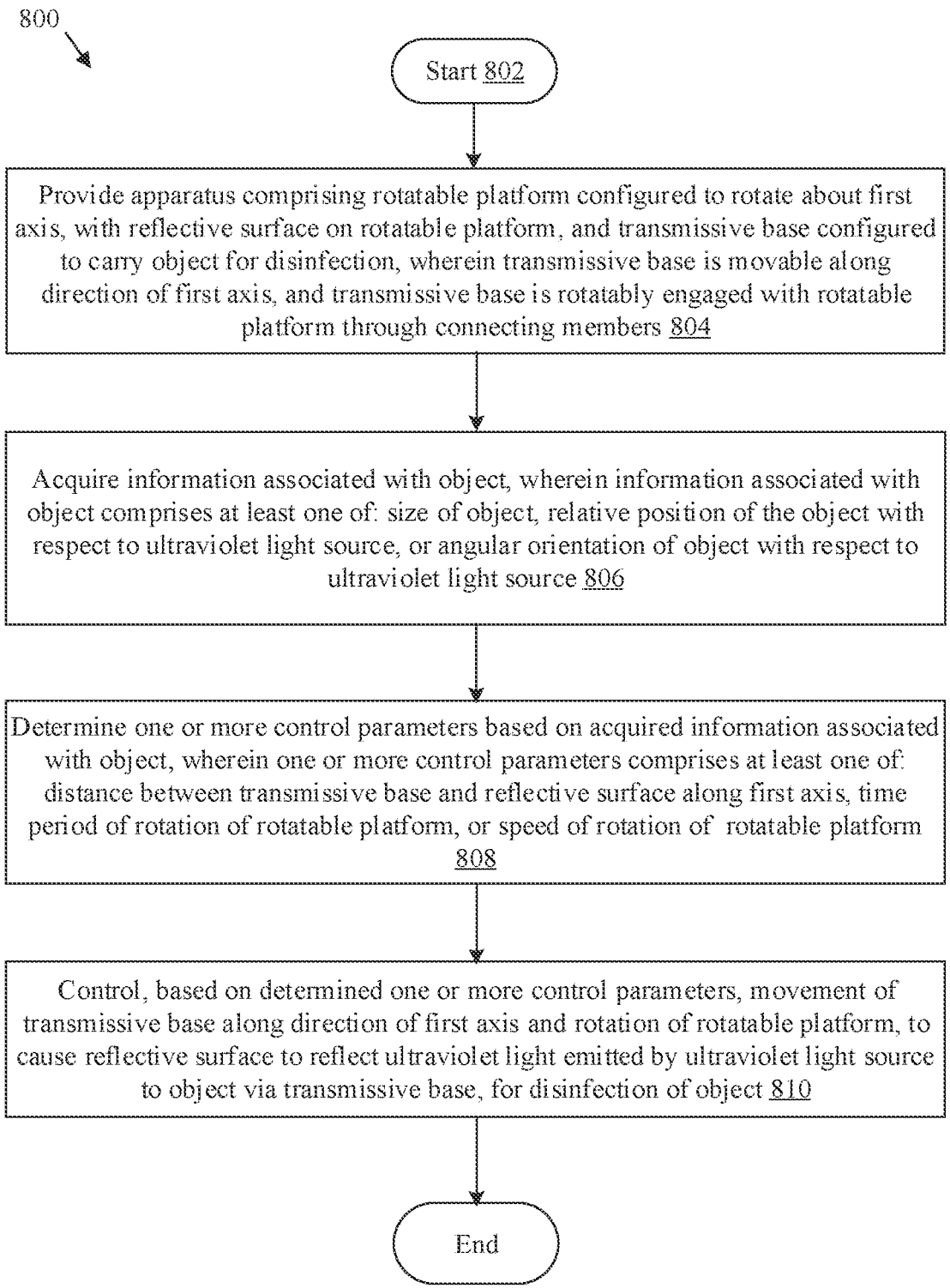
FIG. 8 is a flowchart that illustrates exemplary operations for disinfection of an object by the apparatus of FIG. 1, in accordance with an embodiment of the disclosure.

FIG. 8 is a flowchart that illustrates exemplary operations for disinfection of an object by the apparatus of FIG. 1, in accordance with an embodiment of the disclosure. FIG. 8 is explained in conjunction with elements from FIGS. 1, 2, 3A, 3B, 4, 5A, 5B, 6A, 6B, and 7. With reference to FIG. 8, there is shown a flowchart 800 that depicts a method to disinfect the object 110 carried on the transmissive base 106 of the apparatus 102 of FIG. 1. The method illustrated in the flowchart 800 may start from 802.

At 802, the apparatus 102 comprising the rotatable platform 104 configured to rotate about the first axis 108, the reflective surface 104A on the rotatable platform 104, and the transmissive base 106 that may be configured to carry the object 110 for disinfection may be provided. The transmissive base 106 may be movable along the direction 108A of the first axis 108. The transmissive base 106 may be rotatably engaged with rotatable platform 104 through the connecting members 112.

At 804, the information associated with the object 110 may be acquired. The information associated with the object 110 may include at least one of the size of object 110, the relative position of the object 110 with respect to the ultraviolet light source 116, or the angular orientation of the object 110 with respect to the ultraviolet light source 116. In an embodiment, the apparatus 102 may acquire the information associated with the object 110, as described in FIG. 1.

At 806, the one or more control parameters may be determined based on the acquired information associated with the object 110. The one or more control parameters comprises at least one of the distance 106A between the transmissive base 106 and the reflective surface 104A of the rotatable platform 104 along the first axis 108, the time period of rotation of rotatable platform 104, or the speed of rotation of rotatable platform 104. In an embodiment, the apparatus 102 may be configured to determine the one or more control parameters as described in FIG. 1.

At 808, the movement of the transmissive base 106 along the direction 108A of the first axis 108 and the rotation of the rotatable platform 104 may be controlled based on the determined one or more control parameters, to cause the reflective surface 104A to reflect the ultraviolet light emitted by the ultraviolet light source 116 to the object 110 via the transmissive base 106, for disinfection of object 110. In an embodiment, the apparatus 102 may control the movement of the transmissive base 106 and/or the rotation of the rotatable platform 104, as described in FIGS. 3A, 3B, 4, 5A, 5B, 6A, and 6B.

The flowchart 800 is illustrated as discrete operations, such as 802, 804, 806, and 808. However, in certain embodiments, such discrete operations may be further divided into additional operations, combined into fewer operations, or eliminated, or rearranged depending on the implementation without detracting from the essence of the disclosed embodiments.

Various embodiments of the disclosure may provide a non-transitory, computer-readable medium and/or storage medium, and/or a non-transitory machine readable medium and/or storage medium stored thereon, a set of instructions executable by a machine and/or a computer (for example the apparatus 102) for disinfection of the object 110. The set of instructions may be executable by the machine and/or the computer (for example, the apparatus 102) to perform operations that may include, but are not limited to, acquisition of information associated with the object 110, wherein the information associated with the object 110 may include at least one of the size of the object 110, the relative position of the object 110 with respect to an ultraviolet light source 116, or the angular orientation of the object 110 with respect to the ultraviolet light source 116. The operations may further include determination of the one or more control parameters based on the acquired information associated with the object 110, wherein the one or more control parameters may include at least one of the distance 106A between the transmissive base 106 and the reflective surface 104A along the first axis 108, the time period of rotation of the rotatable platform 104, or the speed of the rotation of the rotatable platform 104. The operations may further include control, based on the determined one or more control parameters, the movement (such as the translation) of the transmissive base 106 along the direction 108A of the first axis 108 and/or the rotation of the rotatable platform 104, to cause the reflective surface 104A to reflect the ultraviolet light emitted by the ultraviolet light source 116 onto the object 110, via the transmissive base 106. Based on the movement of the transmissive base 106 along the direction 108A of the first axis 108 and/or the rotation of the rotatable platform 104, the ultraviolet light from the ultraviolet light source 116 may be irradiated onto all parts of the object 110, via the transmissive base 106. The operations may cause the reflective surface 104A to reflect the ultraviolet light onto one or more portions (such as the underside) of the object 110, which may not be directly exposed to the ultraviolet light source 116, via the transmissive base, thereby effectively disinfecting all portions of the object. The execution of operations may be further described, in FIGS. 3A, 3B, 4, 5A, 5B, 6A, 6B, and 7.

Exemplary aspects of the disclosure may include an apparatus (such as, the apparatus 102) that may include a rotatable platform (such as the rotatable platform 104) configured to rotate about a first axis (such as the first axis 108), a reflective surface (such as the reflective surface 104A) on the rotatable platform 104, a transmissive base (such as the transmissive base 106) that may be configured to carry an object (such as the object 110), and circuitry (such as, the circuitry 202). The transmissive base 106 may be movable along a direction of the first axis 108. The transmissive base 106 may be rotatably engaged with the rotatable platform 104 through one or more connecting members (such as the connecting members 112). In an embodiment, the apparatus 102 may be configured to acquire information associated with the object 110. For example, the information associated with the object 110 may comprise a size of the object 110, a relative position of the object 110 with respect to an ultraviolet light source (such as the ultraviolet light source 116), or an angular orientation of the object 110 with respect to the ultraviolet light source 116. Based on the acquired information, the apparatus 102 may be configured to determine one or more control parameters. For example, the one or more control parameters may comprise at least one of a distance between the transmissive base 106 and the reflective surface 104A along the first axis, a time period of rotation of the rotatable platform 104, or a speed of the rotation of the rotatable platform 104. Based on the determined one or more control parameters (for example, the distance between the transmissive base 106 and the reflective surface 104A), the apparatus 102 may control a movement of the transmissive base 106 along the first axis. Based on the determined one or more control parameters (for example, the time period of rotation of the rotatable platform 104, or the speed of the rotation of the rotatable platform 104), the apparatus 102 may control the rotation of the rotatable platform 104, to cause the reflective surface 104A to reflect an ultraviolet light emitted by the ultraviolet light source 116 onto the object 110, via the transmissive base 106. In accordance with an embodiment, the reflective surface 104A and the transmissive base 106 may be coaxial with the rotatable platform 104.

In accordance with an embodiment, the circuitry 202 may be further configured to control a distance 106A between the transmissive base 106 and the reflective surface 104A along the first axis 108, based on the controlled movement of the transmissive base 106.

In accordance with an embodiment, the apparatus 102 may comprise an actuator (such as the actuator 112A) configured to move the transmissive base 106 along the direction 108A of the first axis 108. The circuitry 202 may be further configured to control the actuator 112A to change the distance 106A between the transmissive base 106 and the reflective surface 104A.

In accordance with an embodiment, the ultraviolet light source 116 may be an ultraviolet lamp. The circuitry 202 may be further configured to transmit a control signal to the ultraviolet light source 116 based on the determined one or more control parameters. The control signal may be configured to control a parameter associated with the ultraviolet light source 116. The parameter may include at least one of the emission time of the ultraviolet light emitted by the ultraviolet light source 116, the angular orientation of the emitted ultraviolet light, the wavelength of the emitted ultraviolet light, or the intensity of the emitted ultraviolet light.

In accordance with an embodiment, the apparatus 102 may comprise a first sensor (such as the first sensor 114) configured to detect the information associated with the object 110. The circuitry 202 may be further configured to control of the first sensor 114 to detect the size of the object 110, the relative position of the object 110 with respect to the ultraviolet light source 116, or the angular orientation of the object 110 with respect to the ultraviolet light source 116. The circuitry 202 may be further configured to acquire the information associated with the object 110 based on the detection by the first sensor 114.

In accordance with an embodiment, the apparatus 102 may comprise a second sensor (such as the second sensor 118) configured to measure an intensity of the ultraviolet light emitted by the ultraviolet light source 116. the circuitry 202 may be further configured to acquire the measured intensity of the ultraviolet light from the second sensor 118. The circuitry 202 may be further configured to control at least one of the time period of the rotation of the rotatable platform 104 or the speed of the rotation of the rotatable platform 104 based on the acquired intensity. The circuitry 202 may be further configured to determine the emission time of the ultraviolet light from the ultraviolet light source 116 based on at least one of the acquired intensity or the wavelength of the emitted ultraviolet light. The circuitry 202 may be further configured to control at least one of the time period of the rotation of the rotatable platform 104 or the speed of the rotation of the rotatable platform 104 based on the determined emission time.

In accordance with an embodiment, the circuitry 202 may be further configured to acquire information associated with the ultraviolet light source 116. The information associated with the ultraviolet light source 116 may include at least one of the location of the ultraviolet light source 116, the angular orientation of the ultraviolet light source 116 with respect to the reflective surface 104A, or the wavelength of the ultraviolet light from the ultraviolet light source 116. The circuitry 202 may be further configured to determine the one or more control parameters based on the acquired information associated with the ultraviolet light source 116.

In accordance with an embodiment, the circuitry 202 may be further configured to control the rotation of the rotatable platform 104 to be one of the continuous rotation or the cyclic rotation.

In accordance with an embodiment, the transmissive base 106 may comprise an ultraviolet transmissive material. The reflective surface may have a concave surface. The concave surface may be configured to reflect the ultraviolet light from the ultraviolet light source 116 as a focused beam on the object 110.

In accordance with an embodiment, the rotatable platform 104 may comprise an actuator (such as the actuator 706) configured to tilt the transmissive base 106 about a second axis (such as the second axis 702) orthogonal to the first axis 108.

The foregoing description of embodiments and examples has been presented for purposes of illustration and description. It is not intended to be exhaustive or limiting to the forms described. Numerous modifications are possible considering the above teachings. Some of those modifications have been discussed and others will be understood by those skilled in the art. The embodiments were chosen and described for illustration of various embodiments. The scope is not limited to the examples or embodiments set forth herein but can be employed in any number of applications and equivalent devices by those of ordinary skill in the art. Rather it is hereby intended the scope be defined by the claims appended hereto. Additionally, the features of various implementing embodiments may be combined to form further embodiments.

For the purposes of the present disclosure, expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural. Further, all joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly. Moreover, such joinder references do not necessarily infer that two elements are directly connected to each other.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted for carrying out the methods described herein may be suited. A combination of hardware and software may be a general-purpose computer system with a computer program that, when loaded and executed, may control the computer system such that it carries out the methods described herein. The present disclosure may be realized in hardware that includes a portion of an integrated circuit that also performs other functions. It may be understood that, depending on the embodiment, some of the steps described above may be eliminated, while other additional steps may be added, and the sequence of steps may be changed.

The present disclosure may also be embedded in a computer program product, which includes all the features that enable the implementation of the methods described herein, and which when loaded in a computer system is able to carry out these methods. Computer program, in the present context, means any expression, in any language, code or notation, of a set of instructions intended to cause a system with an information processing capability to perform a particular function either directly, or after either or both of the following: a) conversion to another language, code or notation; b) reproduction in a different material form. While the present disclosure has been described with reference to certain embodiments, it will be understood by those skilled in the art that various changes may be made, and equivalents may be substituted without departing from the scope of the present disclosure. In addition, many modifications may be made to adapt a situation or material to the teachings of the present disclosure without departing from its scope. Therefore, it is intended that the present disclosure is not limited to the embodiment disclosed, but that the present disclosure will include all embodiments that fall within the scope of the appended claims.

What is claimed is:

1. An apparatus, comprising:
a rotatable platform configured to rotate about a first axis;
a reflective surface on the rotatable platform;
a transmissive base configured to carry an object, wherein
the transmissive base is movable along a direction of the first axis, and
the transmissive base is rotatably engaged with the rotatable platform through connecting members; and
circuitry configured to:
acquire information associated with the object, wherein the information associated with the object comprises at least one of a size of the object, a relative position of the object with respect to an ultraviolet light source, or an angular orientation of the object with respect to the ultraviolet light source;
determine one or more control parameters based on the acquired information associated with the object, wherein the one or more control parameters comprise at least one of a distance between the transmissive base and the reflective surface along the first axis, a time period of rotation of the rotatable platform, or a speed of the rotation of the rotatable platform; and control, based on the determined one or more control parameters, a movement of the transmissive base along the direction of the first axis and the rotation of the rotatable platform, to cause the reflective surface to reflect an ultraviolet light emitted by the ultraviolet light source onto the object, via the transmissive base.

2. The apparatus according to claim 1, wherein the reflective surface and the transmissive base are coaxial with the rotatable platform.

3. The apparatus according to claim 1, wherein the circuitry is further configured to control the distance between the transmissive base and the reflective surface along the first axis based on the controlled movement of the transmissive base.

4. The apparatus according to claim 1, further comprising an actuator configured to move the transmissive base along the direction of the first axis, wherein the circuitry is further configured to control the actuator to change the distance between the transmissive base and the reflective surface.

5. The apparatus according to claim 1, wherein
the ultraviolet light source is an ultraviolet lamp,
the circuitry is further configured to transmit a control signal to the ultraviolet light source based on the determined one or more control parameters,
the control signal is configured to control a parameter associated with the ultraviolet light source, and
the parameter comprises at least one of an emission time of the ultraviolet light emitted by the ultraviolet light source, an angular orientation of the emitted ultraviolet light, a wavelength of the emitted ultraviolet light, or an intensity of the emitted ultraviolet light.

6. The apparatus according to claim 1, further comprising a first sensor configured to detect the information associated with the object, wherein
the circuitry is communicably coupled to the first sensor, and
the circuitry is further configured to:
control the first sensor to detect the at least one of the size of the object, the relative position of the object with respect to the ultraviolet light source, or the angular orientation of the object with respect to the ultraviolet light source; and
acquire the information associated with the object based on the detection by the first sensor.

7. The apparatus according to claim 1, further comprising a second sensor configured to measure an intensity of the ultraviolet light emitted by the ultraviolet light source, wherein
the circuitry is communicably coupled to the second sensor, and
the circuitry is further configured to:
acquire the measured intensity of the ultraviolet light from the second sensor; and
control at least one of the time period of the rotation of the rotatable platform or the speed of the rotation of the rotatable platform based on the acquired intensity.

8. The apparatus according to claim 7, wherein the circuitry is further configured to:
determine an emission time of the ultraviolet light from the ultraviolet light source based on at least one of the acquired intensity or a wavelength of the emitted ultraviolet light; and
control at least one of the time period of the rotation of the rotatable platform or the speed of the rotation of the rotatable platform based on the determined emission time.

9. The apparatus according to claim 1, wherein the circuitry is further configured to:
acquire information associated with the ultraviolet light source, wherein the information associated with the ultraviolet light source comprises at least one of a location of the ultraviolet light source, an angular orientation of the ultraviolet light source with respect to the reflective surface, or a wavelength of the ultraviolet light from the ultraviolet light source; and
determine, based on the acquired information associated with the ultraviolet light source, the one or more control parameters.

10. The apparatus according to claim 1, wherein the transmissive base comprises an ultraviolet transmissive material.

11. The apparatus according to claim 1, wherein
the reflective surface has a concave surface, and
the concave surface is configured to reflect the ultraviolet light from the ultraviolet light source as a focused beam on the object.

12. The apparatus according to claim 1, wherein the rotatable platform comprises an actuator configured to control at a tilt of the transmissive base about a second axis orthogonal to the first axis.

13. The apparatus according to claim 1, wherein the circuitry is further configured to control the rotation of the rotatable platform to be one of a continuous rotation or a cyclic rotation.

* * * * *